United States Patent
Bai et al.

(10) Patent No.: US 10,070,661 B2
(45) Date of Patent: *Sep. 11, 2018

(54) FEEDBACK CONTROL OF FOOD TEXTURE SYSTEM AND METHOD

(71) Applicant: Frito-Lay North America, Inc., Plano, TX (US)

(72) Inventors: Ou Bai, Plano, TX (US); Wilfred Marcellien Bourg, Jr., Melissa, TX (US); Scott Fagan, Dallas, TX (US); Enrique Michel-Sanchez, Dallas, TX (US); Shahmeer Ali Mirza, Dallas, TX (US); Scott G. Richardson, Gainesville, TX (US); Chen C. Shao, Plano, TX (US)

(73) Assignee: FRITO-LAY NORTH AMERICA, INC., Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/864,728

(22) Filed: Sep. 24, 2015

(65) Prior Publication Data

US 2017/0086479 A1 Mar. 30, 2017

(51) Int. Cl.
*G01N 33/02* (2006.01)
*A23L 19/18* (2016.01)
(Continued)

(52) U.S. Cl.
CPC ............ *A23L 19/18* (2016.08); *G01N 29/041* (2013.01); *G01N 29/14* (2013.01);
(Continued)

(58) Field of Classification Search
CPC .... A21C 11/16; A21C 11/22; G06Q 10/0832; A23L 3/003; A23B 7/148; A23B 7/152;
(Continued)

(56) References Cited

U.S. PATENT DOCUMENTS

| 4,169,662 A | * | 10/1979 | Kaule | .............. G01N 29/221 |
| | | | | 181/142 |
| 4,184,768 A | * | 1/1980 | Murphy | .......... G01N 21/1702 |
| | | | | 250/252.1 |

(Continued)

FOREIGN PATENT DOCUMENTS

| DE | 329319 | 11/1920 |
| DE | 3939411 | 6/1991 |

(Continued)

OTHER PUBLICATIONS

Slaughter, "Nondestructive Quality of Measurement of Horticultural Crops," University of CA, Davis, 2011, 13 pages.

(Continued)

*Primary Examiner* — Eric Stapleton
(74) *Attorney, Agent, or Firm* — Colin P. Cahoon; Sudhakar V. Allada; Carstens & Cahoon, LLP

(57) ABSTRACT

A feedback and feedforward as well as a statistical predictive control system and method for continuously controlling texture of a food snack in a manufacturing process. The feedback system includes a quantitative texture measuring tool that is positioned downstream of a food processing unit. The texture measuring tool continuously measures a texture attribute of food snack from the food processing unit and feeds back texture attribute information to a controller that controls input parameters to food processing unit such that the texture attribute of a resultant food snack falls within an acceptable limit. The texture measuring tool comprises an excitation tool that strikes the food snack and produces an acoustic signal that is processed by a data processing unit. The data processing unit identifies relevant frequencies in the acoustic signal and quantitatively measures a texture attribute based on a correlated model that includes the relevant frequencies.

22 Claims, 17 Drawing Sheets

(51) Int. Cl.
*G01N 29/04* (2006.01)
*G01N 29/44* (2006.01)
*G01N 33/10* (2006.01)
*G01N 29/14* (2006.01)
*G01N 29/24* (2006.01)

(52) U.S. Cl.
CPC ..... *G01N 29/2418* (2013.01); *G01N 29/4445* (2013.01); *G01N 33/10* (2013.01); *A23V 2002/00* (2013.01); *G01N 2291/023* (2013.01); *G01N 2291/02466* (2013.01); *G01N 2291/2638* (2013.01)

(58) Field of Classification Search
CPC .......... G01N 3/40; G01N 29/14; G01N 29/46; G01N 19/00; G01N 33/02; G01N 2203/0087; G01N 2291/02466; G01N 2291/028; A21B 7/005; F26B 15/18; F26B 2210/06
USPC ......... 99/348, 325, 486, 353, 646, 468, 474, 99/477; 73/863.52, 863, 863.54, 863.81, 73/863.82, 861.73, 864.82; 702/2, 1, 22, 702/31, 32; 356/300, 301
See application file for complete search history.

(56) References Cited

U.S. PATENT DOCUMENTS

| | | | | |
|---|---|---|---|---|
| 4,187,026 A * | 2/1980 | Schaffer | G01J 5/42 | 250/338.1 |
| 4,234,258 A * | 11/1980 | Frosch | G01N 21/1702 | 250/343 |
| 4,236,827 A * | 12/1980 | Horiba | G01N 21/37 | 250/343 |
| 4,325,252 A * | 4/1982 | Miller | G01K 17/003 | 250/338.1 |
| 4,381,148 A * | 4/1983 | Ulrich | G01J 5/42 | 356/213 |
| 4,479,265 A * | 10/1984 | Muscatell | H04R 27/00 | 359/285 |
| 4,562,736 A | 1/1986 | Iwasaki et al. | | |
| 4,866,283 A | 9/1989 | Hill | | |
| 4,899,589 A * | 2/1990 | Thompson | G01N 29/07 | 73/597 |
| 5,048,340 A * | 9/1991 | Thompson | G01N 29/07 | 73/597 |
| 5,070,733 A | 12/1991 | Nagata | | |
| 5,121,426 A * | 6/1992 | Baumhauer, Jr. | H04M 1/20 | 379/388.02 |
| 5,152,401 A * | 10/1992 | Affeldt, Jr. | G01N 3/405 | 209/556 |
| 5,226,076 A * | 7/1993 | Baumhauer, Jr. | H04M 1/19 | 379/419 |
| 5,251,486 A * | 10/1993 | Thompson | G01N 29/07 | 73/597 |
| 5,286,313 A * | 2/1994 | Schultz | G10K 15/046 | 148/508 |
| 5,372,030 A | 12/1994 | Prussia | | |
| 5,526,689 A | 6/1996 | Coulter et al. | | |
| 5,588,428 A | 12/1996 | Smith | | |
| 5,691,473 A * | 11/1997 | Peleg | G01N 3/32 | 209/599 |
| 5,751,416 A * | 5/1998 | Singh | G01J 3/30 | 356/300 |
| 5,780,724 A | 7/1998 | Olender | | |
| 5,804,727 A * | 9/1998 | Lu | G01H 5/00 | 73/159 |
| 5,825,898 A * | 10/1998 | Marash | G01S 7/2813 | 381/92 |
| 5,827,974 A | 10/1998 | Nussinovitch | | |
| 5,848,172 A * | 12/1998 | Allen | H04R 1/406 | 381/356 |
| 5,922,387 A * | 7/1999 | Parada | A23L 19/13 | 426/451 |
| 6,034,768 A * | 3/2000 | Fraser | G01N 21/67 | 216/60 |
| 6,057,927 A * | 5/2000 | Levesque | G01B 11/18 | 356/432 |
| 6,122,389 A * | 9/2000 | Grosz | H04R 1/38 | 381/338 |
| 6,276,536 B1* | 8/2001 | Terasaki | G01N 29/045 | 209/556 |
| 6,311,558 B1* | 11/2001 | Clark | G01L 1/12 | 73/597 |
| 6,385,558 B1* | 5/2002 | Schlemm | G05B 23/0227 | 702/182 |
| 6,407,811 B1* | 6/2002 | Snyder | G01J 3/443 | 356/316 |
| 6,466,309 B1* | 10/2002 | Kossakovski | G01N 21/718 | 356/318 |
| 6,494,098 B1* | 12/2002 | Leybovich | G01N 29/11 | 73/579 |
| 6,531,707 B1* | 3/2003 | Favreau | G01N 21/8901 | 250/559.46 |
| 6,532,821 B2* | 3/2003 | Lamouche | G01N 29/2418 | 73/602 |
| 6,539,781 B1* | 4/2003 | Crezee | G01N 3/405 | 73/573 |
| 6,628,404 B1* | 9/2003 | Kelley | H05B 6/06 | 356/502 |
| 6,657,721 B1* | 12/2003 | Palleschi | G01N 21/718 | 356/318 |
| 6,694,173 B1 | 2/2004 | Bende | | |
| 6,753,957 B1* | 6/2004 | Graft | G01N 21/718 | 356/318 |
| 6,771,368 B1* | 8/2004 | Chadwick | G01N 21/718 | 356/317 |
| 6,792,324 B2 | 9/2004 | Trinkel | | |
| 6,823,736 B1 | 11/2004 | Brock | | |
| 6,857,317 B2* | 2/2005 | Sakurai | G01N 29/12 | 426/231 |
| 6,909,505 B2* | 6/2005 | Lucas | G01N 21/718 | 250/339.01 |
| 6,944,204 B2* | 9/2005 | Zhou | G01N 21/718 | 356/300 |
| 6,987,564 B2* | 1/2006 | Gornushkin | G01J 3/44 | 356/301 |
| 7,092,807 B2* | 8/2006 | Burk | F16H 59/66 | 701/51 |
| 7,165,451 B1 | 1/2007 | Brooks | | |
| 7,195,731 B2* | 3/2007 | Jones | C08L 63/00 | 264/109 |
| 7,595,463 B2* | 9/2009 | Weick | B23K 26/032 | 219/121.62 |
| 7,692,788 B2 | 4/2010 | Popp | | |
| 7,802,477 B2* | 9/2010 | Sakurai | G01N 3/405 | 73/579 |
| 7,860,277 B2 | 12/2010 | Mulder | B07C 5/3422 | 382/110 |
| 8,319,964 B2* | 11/2012 | Hahn | G01N 21/718 | 356/318 |
| 8,368,289 B2 | 2/2013 | Karabutov et al. | | |
| 8,567,250 B2 | 10/2013 | Loeser | | |
| 8,619,255 B2* | 12/2013 | Gennadievich | G01N 21/718 | 356/318 |
| 8,638,956 B2* | 1/2014 | Deng | H04R 1/38 | 367/178 |
| 8,659,753 B1* | 2/2014 | Cabalo | G01J 1/4257 | 356/213 |
| 8,891,073 B2* | 11/2014 | Effenberger, Jr. | G01J 3/18 | 356/318 |
| 9,032,798 B2* | 5/2015 | Sakakibara | G01N 3/40 | 73/12.01 |
| 9,068,926 B2 | 6/2015 | Schade | | |
| 9,159,126 B2* | 10/2015 | Johnson | A22C 17/008 | |
| 9,285,310 B2* | 3/2016 | Patel | G01N 21/39 | |
| 9,358,636 B2* | 6/2016 | Hammann | B23K 26/03 | |
| 9,541,537 B1* | 1/2017 | Bai | G01N 33/10 | |

(56) References Cited

U.S. PATENT DOCUMENTS

| | | | | |
|---|---|---|---|---|
| 2002/0039186 | A1* | 4/2002 | Rosenberg | G01J 3/02 356/432 |
| 2003/0095266 | A1* | 5/2003 | Detalle | G01N 21/718 356/502 |
| 2003/0216875 | A1* | 11/2003 | Sakurai | G01N 29/12 702/56 |
| 2004/0197012 | A1* | 10/2004 | Bourg, Jr. | G01N 21/8851 382/110 |
| 2007/0218556 | A1* | 9/2007 | Harris | G01N 21/274 436/25 |
| 2007/0229834 | A1* | 10/2007 | Patel | G01J 3/42 356/432 |
| 2008/0003339 | A1* | 1/2008 | Johnson | A23P 10/35 426/534 |
| 2008/0092674 | A1* | 4/2008 | Sakurai | G01N 3/405 73/866.5 |
| 2008/0093775 | A1* | 4/2008 | Menoni | B23K 26/032 264/400 |
| 2008/0124433 | A1* | 5/2008 | Yelden | A23L 5/00 426/233 |
| 2008/0204757 | A1 | 8/2008 | Manning | |
| 2008/0253648 | A1* | 10/2008 | Mulder | B07C 5/3422 382/165 |
| 2009/0316927 | A1* | 12/2009 | Ferrill | H04R 1/02 381/91 |
| 2010/0070197 | A1* | 3/2010 | Wang | G01J 3/02 702/22 |
| 2010/0297671 | A1 | 11/2010 | Tschmelak | |
| 2011/0033062 | A1* | 2/2011 | Deng | H04R 3/005 381/92 |
| 2012/0002193 | A1* | 1/2012 | Elliott | G01K 17/003 356/121 |
| 2012/0008802 | A1* | 1/2012 | Felber | H03G 3/24 381/107 |
| 2012/0014534 | A1* | 1/2012 | Bodley | H04N 7/15 381/77 |
| 2012/0020485 | A1* | 1/2012 | Visser | H04R 3/005 381/57 |
| 2012/0099732 | A1* | 4/2012 | Visser | G10L 21/0272 381/17 |
| 2012/0202277 | A1 | 8/2012 | Wagner et al. | |
| 2012/0206722 | A1* | 8/2012 | Grigoropoulos | G01N 21/718 356/318 |
| 2012/0234102 | A1* | 9/2012 | Johnson | G01N 3/08 73/826 |
| 2012/0314214 | A1* | 12/2012 | Alexander | G01J 3/443 356/318 |
| 2013/0058514 | A1* | 3/2013 | Akino | H04R 1/283 381/346 |
| 2013/0118227 | A1* | 5/2013 | Sakakibara | G01N 3/40 73/12.01 |
| 2013/0150114 | A1* | 6/2013 | Bodley | H04M 3/568 455/517 |
| 2013/0201316 | A1* | 8/2013 | Binder | H04L 67/12 348/77 |
| 2013/0228016 | A1* | 9/2013 | Sakurai | G01N 3/405 73/661 |
| 2013/0266925 | A1* | 10/2013 | Nunamaker, Jr. | G09B 7/00 434/362 |
| 2013/0344208 | A1* | 12/2013 | Singh | H05B 6/647 426/243 |
| 2014/0011690 | A1* | 1/2014 | Dimov | C12N 15/1065 506/9 |
| 2014/0033819 | A1 | 2/2014 | Loeser et al. | |
| 2014/0079248 | A1 | 3/2014 | Short | |
| 2014/0125965 | A1* | 5/2014 | Nagli | G01N 21/3103 356/4.01 |
| 2015/0204822 | A1 | 7/2015 | Horan | |
| 2017/0027168 | A1* | 2/2017 | Heath | A01N 25/30 |
| 2017/0086479 | A1* | 3/2017 | Bai | A23L 1/025 |
| 2017/0089869 | A1* | 3/2017 | Bai | G01N 29/4445 |
| 2017/0097222 | A1* | 4/2017 | Bai | G01B 5/28 |
| 2017/0097324 | A1* | 4/2017 | Bai | G01N 29/2418 |
| 2017/0176309 | A1* | 6/2017 | Bai | G01N 3/32 |
| 2017/0184551 | A1* | 6/2017 | Bai | G01N 29/2418 |
| 2018/0011069 | A1* | 1/2018 | Bai | G01N 33/10 |

FOREIGN PATENT DOCUMENTS

| | | |
|---|---|---|
| DE | 19716672 | 6/1998 |
| DE | 69320728 | 1/1999 |
| DE | 10315541 | 10/2001 |
| DE | 10205051643 | 4/2006 |
| DE | 102006035730 | 1/2008 |
| EP | 1348955 | 10/2003 |
| ES | 2147141 | 8/2000 |
| JP | 2006227021 A | 8/2006 |
| JP | 2009008696 | 1/2009 |
| UA | 104233 | 1/2014 |
| WO | 9425851 | 11/1994 |
| WO | 9857145 | 12/1998 |
| WO | 9915890 | 4/1999 |
| WO | 02057774 | 7/2002 |
| WO | 02079765 | 10/2002 |
| WO | 2009047549 | 4/2009 |
| WO | 2013004210 | 1/2013 |
| WO | 2013027445 A1 | 2/2013 |
| WO | 2014180568 | 11/2014 |

OTHER PUBLICATIONS

Ravishankar, et al., "Photo-acoustic emission measurements in liquid-based food and aqueous products," 2007, 12 pages.

PCT International Search Report and Written Opinion for PCT/US2015/052510 dated Dec. 14, 2015 (9 pages).

Kowalczyk et al., "Bulk measurement of copper and sodium content in CuIn0.7Ga0.3Se2 (CIGS) solar cells with nanosecond pulse length laser induced breakdown spectroscopy (LIBS)" Department of Physics and Astronomy, University of Hawaii, Jan. 8, 2013 (6 pages).

Pedarnig, "Application of laser-induced breakdown spectroscopy to the analysis of secondary materials in industrial production" 2014 Woodhead Publishing Limited (26 pages).

Abdel-Salam et al., "Qualitative evaluation of maternal milk and commercial infant formulas via LIBS" Talanta 115 (2013) 422-426 (5 pages).

Kongbonga et al., Classification of vegetable oils based on their concentration of saturated fatty acids using laser induced breakdown spectroscopy (LIBS), Food Chemistry 147 (2014) 327-331 (5 pages).

Lei et al., "Time-resolved characterization of laser-induced plasma from fresh potatoes" Spectrochimica Acta Part B 64 (2009) 891-898 (8 pages).

Applied Spectra, Inc.—Technique—Gate Delay, from http://www.appliedspectra.com/technology/gate-delay.html printed Sep. 29, 2014 (6 pages).

Lanza et al., "Calibrating the ChemCam laser-induced breakdown spectroscopy instrument for carbonate minerals on Mars" May 1, 2010, vol. 49, No. 13, Applied Optics (7 pages).

NRC-CNRC "Laser-Induced Breakdown Spectroscopy (LIBS) Optical Sensing Technology for Rapid On-site Chemical Analysis" (4 pages).

What is LIBS from http://www.spectrolabsystems.net/products/analytical-instruments/laser-induced-breakdown . . . , printed Aug. 6, 2014 (1 page).

TSI Laser Induced Breakdown Spectroscopy, Chemreveal LIBS Desktop Elemental Analyzer from http://www.tsi.com/ChemReveal-LIBS-Desktop-Analyzer/, printed Aug. 6, 2014 (3 pages).

Sun et al., "Correction of self-absorption effect in calibration-free laser-induced breakdown spectroscopy by an internal reference method" Talanta 79 (2009) 388-395 (8 pages).

Assion et al., "Femtosecond laser-induced-breakdown spectrometry for Ca2+ analysis of biological samples with hig spatial resolution," Appl Phys. 2003, 77:391-97.

(56) References Cited

OTHER PUBLICATIONS

Menut et al., "Micor-laser-induced breakdown spectroscopy technique: a powerful method for performing quantitative surface mapping on conductive and nonconductive samples," Oct. 2003, Applied Optics, vol. 42, No. 3 0, pp. 6063-6071.
Samek et al., "Ultra-short laser puls ablation using shear-force feedback: Femtosecond laser induced breakdown spectroscopy feasability study," Spectrochimica Acta Part B, pp. 1225-1229.
Berer et al., "Remote photoacoustic imaging for material inspection" 2nd International Symposium on Laser-Ultrasonics—Science, Technology and Applications, Journal of Physics: Conference Series 278 (2011) 012034 (4 pages).
Cravetchi et al., "Scanning microanalysis of Al alloys by laser-induced breakdown spectroscopy" Spectrochimica Acta Part B 59 (2004) 1439-1450 (12 pages).
Kossakovski et al., "Topographical and Chemical Microanalysis of Surfaces with a Scanning Probe Microscope and Laser-Induced Breakdown Spectroscopy" Anal. Chem. 2000, 72, 4731-4737 (7 pages).

\* cited by examiner

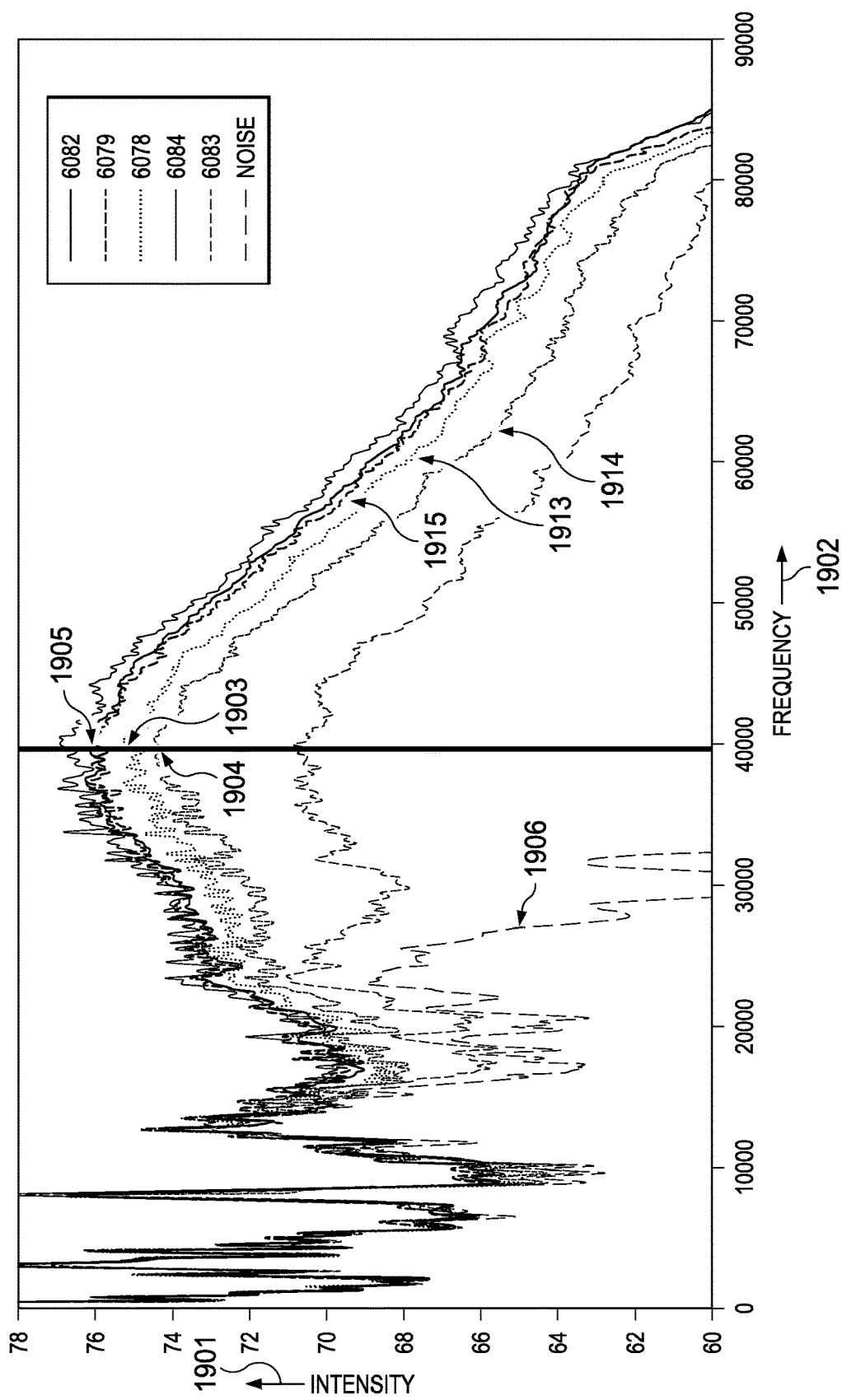

FEEDBACK CONTROL OF FOOD TEXTURE SYSTEM AND METHOD

FIELD OF THE INVENTION

The present invention relates to a continuous feedback control of texture for food products using quantitative photo acoustic techniques in a food manufacturing system.

PRIOR ART AND BACKGROUND OF THE INVENTION

Prior Art Background

Texture is one of the most important sensory characteristics that determine consumer preference for food products and is usually assessed by sensory evaluation. However, sensory evaluation is time-consuming and expensive, and therefore, reliable and practical instrumental methods are needed to accurately predict sensory texture attributes and other food snack properties.

When a food snack such as potato chip is manufactured, textural properties are dependent on raw material characteristics (i.e. low solids or high solids potatoes) and the processing conditions that the raw material undergoes such as temperature profile, slice thickness, moisture content, etc.

The crispiness, softness and/or crunchiness of a potato chip are just a few examples of texture and mouthfeel characteristics that make food appealing and satisfying to consumers. Texture is one of the major criteria which consumers use to judge the quality and freshness of many foods. When a food produces a physical sensation in the mouth (hard, soft, crisp, moist, dry), the consumer has a basis for determining the food's quality (fresh, stale, tender, ripe)

A major challenge is how to accurately and objectively measure texture and mouthfeel. Texture is a composite property related to a number of physical properties (e.g., hardness and fracturability), and the relationship is complex. Texture or mouthfeel cannot be quantitatively measured in a single value obtained from an instrument. Mouthfeel is hard to define as it involves food's entire physical and chemical interaction in the mouth—from initial perception on the palate, to first bite, through mastication and finally, the act of swallowing. There is a need to quantitatively measure the food interaction in the mouth.

A problem with hardness is that their correlations with sensory tests are not always as high as expected. In this many instances, the metric of peak force exerted on a potato chip does not adequately replicate the energy experienced by consumers. Therefore, consumers' judgments of hardness can be more nuanced than a simple peak force metric from a destructive analytical test.

Presently, there is no good correlation of any type between instrument readings and taste panel scores. The issue is that no instrument is capable of manipulating a food product precisely the same way as the human mouth during mastication. For example, an instrument may compress a food product between two plates, while a human would be biting down with incisors. Therefore, there is a need for a quantitative texture measurement that has a good correlation with a qualitative measurement from an expert panel.

Prior Art Food Snack Manufacturing System (0100)

As illustrated in FIG. 1, a prior art food snack manufacturing system comprises a series of apparatus that include a sourcing stage (0101), storage station (0102), wash/peel station (0103), slicing station (0104), frying station (0105), inspection station (0106) and a packaging station (0107). The food snacks, such as potato chips, may be conveyed from station to station on a conveyor belt in the manufacturing system.

Prior Art Food Snack Manufacturing Method (0110)

As generally shown in FIG. 1a, a prior art manufacturing method associated with the prior art system in FIG. 1 may include the steps comprising:
(1) Sourcing food ingredients (0111);
  Ingredients for food snacks, for example, potatoes may be sourced from different farms.
(2) Storing food ingredients (0112);
  When the potatoes arrive at the plant, they are examined and tasted for quality. A half dozen or so buckets are randomly filled. Some are punched with holes in their cores so that they can be tracked through the cooking process. The potatoes are examined for green edges and blemishes. The pile of defective potatoes is weighed; if the weight exceeds a company's preset allowance, the entire truckload can be rejected. The potatoes are loaded into a vertical helical screw conveyer which allows stones to fall to the bottom and pushes the potatoes up to a conveyer belt to the automatic peeling machine. After they have been peeled, the potatoes are washed with cold water
(3) Processing food ingredients (0113);
  The potatoes pass through a revolving impaler/presser that cuts them into paper-thin slices. The slices fall into a second cold-water wash that removes the starch released when the potatoes are cut. The slices pass under air jets that remove excess water as they flow into troughs filled with oil. The oil temperature is kept at 350-375° F. (176.6-190.5° C.). Paddles gently push the slices along. As the slices tumble, salt is sprinkled from receptacles positioned above the trough.
(4) Inspecting food snack for quality (0114);
  At the end of the trough, a wire mesh belt pulls out the hot chips. As the chips move along the mesh conveyer belt, excess oil is drained off and the chips begin to cool. They then move under an optical sorter that picks out any burnt slices and removes them with puffs of air. The potato chips are inspected for texture by using a qualitative tasting process as described in FIG. 2 (0200).
(5) Determining if the quality is acceptable, if so, proceeding to step (8) (0115);
  Taste samples are made from each batch throughout the manufacturing process, usually at a rate of once per hour. The tasters check the chips for salt, seasoning, moisture, color, and overall flavor. Color is compared to charts that show acceptable chip colors. Texture is also qualitatively determined by tasters as compared to a reference sample. There is a need for an automated in-line texture measurement apparatus to provide an automatic continuous closed loop feedback to control input parameters of the processing step of the manufacturing process.
(6) If food quality not acceptable, rejecting the food snack, proceeding to step (0117) (0116);
(7) Manually adjusting process parameters and proceeding to step (3) (0117); and The process parameters are adjusted manually. Therefore, there needs to be an automatic feedback process that adjusts the input parameters to adjust the output quality such as texture attributes which include hardness, fracturability and denseness
(8) Accepting the food snack (0118).

Prior Art in-Line Qualitative Texture Measurement Method

As generally shown in FIG. 2, a prior art in-line qualitative texture measurement method as described in step (0115) may include the steps comprising:
(1) Tasting a food snack from the output of a food processing unit at the inspection stage (0201);
(2) Comparing the taste to a known reference food snack sample (0202); and
(3) Qualitatively assessing the texture attributes based on mouth feel of the output and a reference sample (0203). The qualitative assessment of texture based on a reference sample taste is subjective and prone to variability. Therefore, there is a need for an objective analytical method to quantitatively measure texture attributes.

Prior Art Texture Correlation Method

As generally shown in FIG. 3, a prior art texture correlation method may include the steps comprising:
(1) shipping food snack samples to an expert panel (0301);
The shipping of the food snack samples may take time and the food snack may undergo texture change during the shipping process. Therefore, there is a need to limit the number of times food snacks are shipped the expert panel.
(2) Qualitatively analyzing the food snack samples (0302);
The process starts with a well-trained sensory panel to carry out a meaningful texture profile analysis, a panel of judges needs to have prior rating knowledge of the texture classification system, the use of standard rating scales and the correct procedures related to the mechanics of testing. Panelist training starts with a clear definition of each attribute. Furthermore, the techniques used to evaluate the food product should be explicitly specified, explaining how the food product is placed in the mouth, whether it is acted upon by the teeth (and which teeth) or by the tongue and what particular sensation is to be evaluated. Panelists are given reference standards for evaluation so they can practice their sensory evaluation techniques and the use of scales. Hardness and fracturability are usually considered to be the most important texture attribute. Presently there is no good correlation of any type between instrument readings and taste panel scores. Presently there are no instruments capable of manipulating a food product precisely the same way as the human mouth during mastication. For example, an instrument may compress a food product between two plates, while a human would be biting down with incisors. In fact, what an instrument measures may not relate at all to what the tongue perceives. Therefore, there is a need to have a system that can quantitatively measure texture attributes and correlate to the taste panel scores.
(3) assigning a descriptive panel number for the texture attributes of the food snack sample (0303);

A organoleptic sensory evaluation is performed in which the trained panelists assign intensity levels on various descriptors/texture attributes. For example, for evaluating the potato chips, hardness may be considered one important attribute. In this case, panelists assign a hardness score based on a scale, where 1 equals extremely soft and 9 equals extremely hard. The panelists may rate the hardness of potato chip samples A, B and C's. After taste paneling is complete, instrument readings of the food product are made as described below in step (0304).
(4) Measure texture attributes using an invasive analytical method (0304);
There is a need that the instrumental technique selected duplicates as closely as possible how the mouth manipulates the particular food product. The instrument should apply the same amount of force in the same direction and at the same rate as the mouth and teeth do during mastication. The instrument may record acoustic signals for a period of time and generate a model. However, current instruments are limited by recording acoustics at discrete frequencies such as between 4000 and 8000 kHz. Therefore, there is a need for recording sound in a wider frequency range.
(5) Correlate the analytical and the qualitative texture attributes (0305); and
Statistically correlate between sensory data (descriptive panel number) and instrumental measurements. Currently, correlation based on Intensity vs. Time measurements, generate a weak correlation statistically. For example, prior art adjusted $R^2$ correlation numbers are in the range of 0.5-0.65 with the time domain acoustic model. Therefore, there is a need for a strong correlation between descriptive panel number and the analytical model.
(6) Generating a correlation model (0306).
Current objective methods to measure texture are limited in detecting textural changes of a small magnitude with an acceptable degree of accuracy and require several measurements of the same substrate to differentiate slightly different substrate with statistical significance.

Consequently, there is a need for a non-invasive quantitative texture measurement that accomplishes the following objectives:
Provide for quantitative analytical measurement of the textural attributes such as hardness and fracturability.
Provide for analyzing frequency domain data to accurately model the texture attributes.
Provide for acoustic signal capture in a broad frequency range.
Provide for shape independent quantitative test for texture measurement.
Provide for quantitative measurement of texture with minimum samples.
Provide for quantitative measurement of texture with minimum samples with greater accuracy and reliability
Provide for a less expensive quantitative texture measurement test.
Provide for instant results of the quantitative measurement with a closed loop feedback control
Provide for a feed forward system that predicts food snack output characteristics based on input food ingredient properties.
Provide for an integrated apparatus to control both moisture and texture attributes of a food snack.

Provide for an accurate texture model to predict texture of a food snack with good correlation with an $R^2$ greater than 0.9.

Provide for high resolution texture measurement with better than 5% accuracy.

Provide for repeatable and reproducible quantitative measurements of food snacks.

Provide for automated method for measuring texture.

While these objectives should not be understood to limit the teachings of the present invention, in general these objectives are achieved in part or in whole by the disclosed invention that is discussed in the following sections. One skilled in the art will no doubt be able to select aspects of the present invention as disclosed to affect any combination of the objectives described above.

BRIEF SUMMARY OF THE INVENTION

The present invention in various embodiments addresses one or more of the above objectives in the following manner. A feedback system for continuously controlling texture of a food snack in a manufacturing process. The feedback system includes a quantitative texture measuring tool that is positioned downstream a food processing unit. The texture measuring tool continuously measures a texture attribute of food snack from the food processing unit and feeds back texture attribute information to a controller. The controller controls plural input parameters to the food processing unit based on the measured texture attribute information, such that the resultant texture attribute of a food snack from the food processing unit falls within an acceptable limit. The texture measuring tool comprises an excitation tool that strikes the food snack and produces an acoustic signal that is forwarded to a data processing unit. The data processing unit smoothens, transforms and filters the signal and identifies relevant frequencies in the acoustic signal. The data processing unit quantitatively measures a texture attribute based on a correlated model that includes the relevant frequencies.

The present invention system may be utilized in the context of method of controlling texture of a snack food in a manufacturing process, the method comprises the steps of:
(1) processing food ingredients in a food processing unit to produce the food snack;
(2) measuring a texture attribute of the food snack with a texture measuring tool;
(3) determining if the texture attribute is within an acceptable limit, if so, proceeding to step (6);
(4) if the texture attribute is outside an acceptable limit in step (3), rejecting the food snack;
(5) feeding back texture attribute information to a controller to adjust input parameters to the food processing unit, proceeding to step (1); and
(6) accepting the food snack and proceeding to step (1).

Integration of this and other preferred exemplary embodiment methods in conjunction with a variety of preferred exemplary embodiment systems described herein in anticipation by the overall scope of the present invention.

BRIEF DESCRIPTION OF THE DRAWINGS

For a fuller understanding of the advantages provided by the invention, reference should be made to the following detailed description together with the accompanying drawings wherein:

FIG. 19 is another exemplary Intensity (dB) vs. Frequency chart for a potato chip with various input ingredient properties according to a preferred embodiment of the present invention.

DESCRIPTION OF THE PRESENTLY EXEMPLARY EMBODIMENTS

Figure 1:
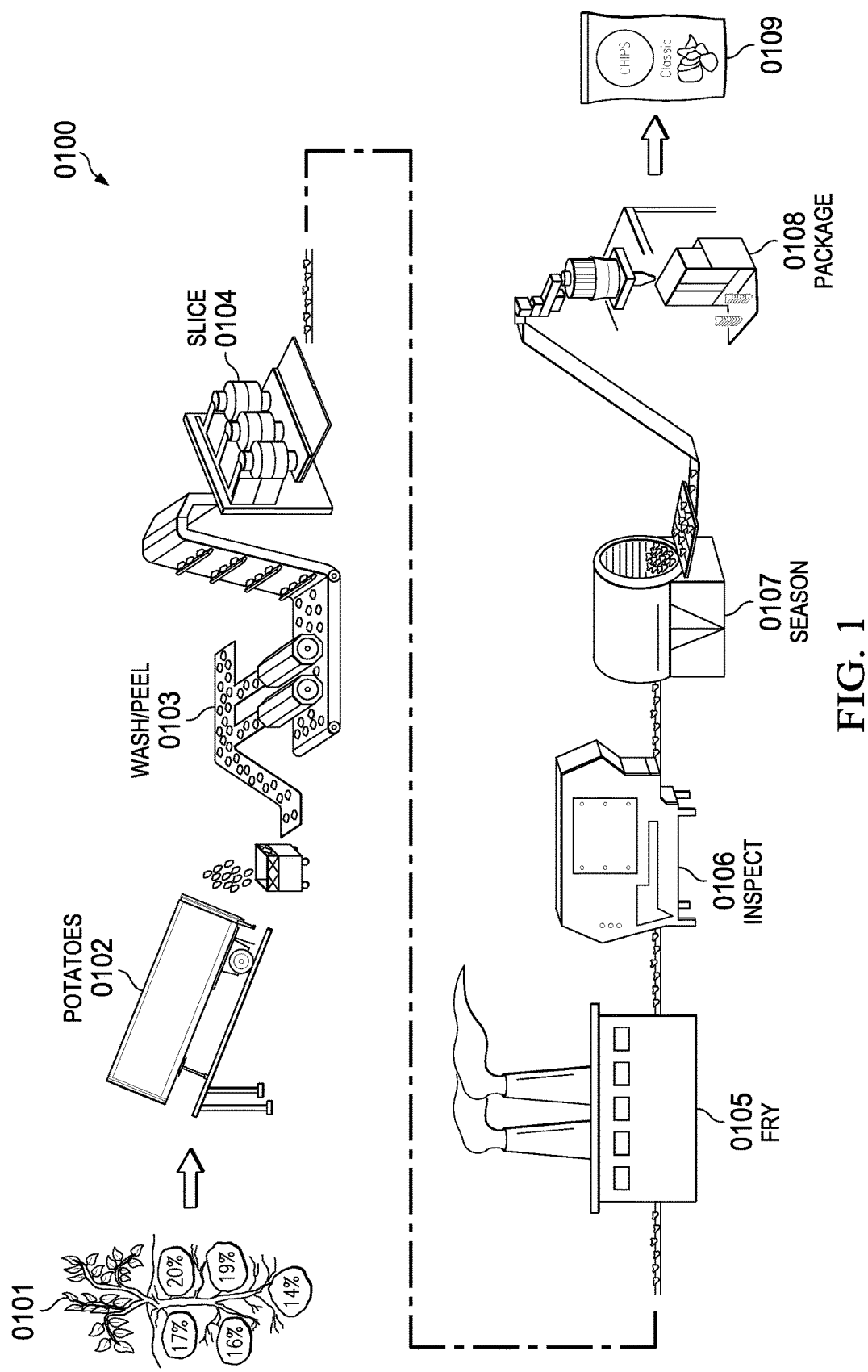
FIG. 1 is a prior art food product manufacturing system.
Figure 1A:
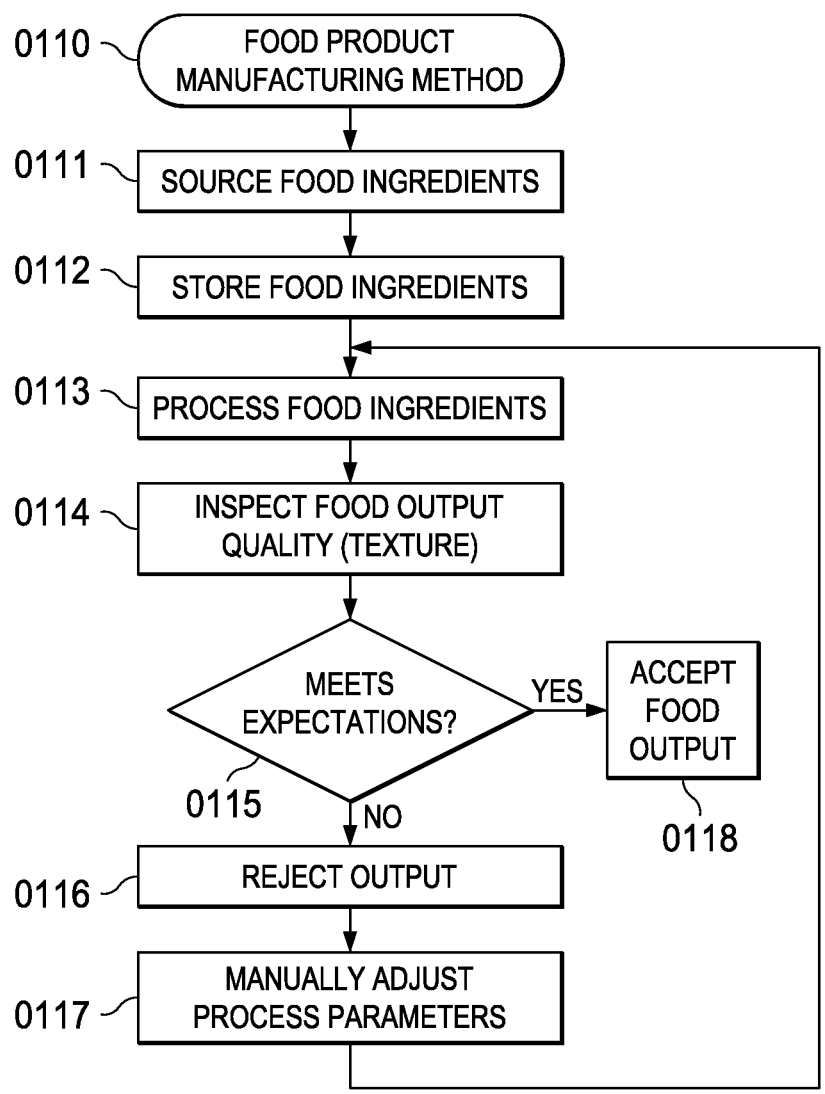
FIG. 1a is a prior art food product manufacturing method.
Figure 2:
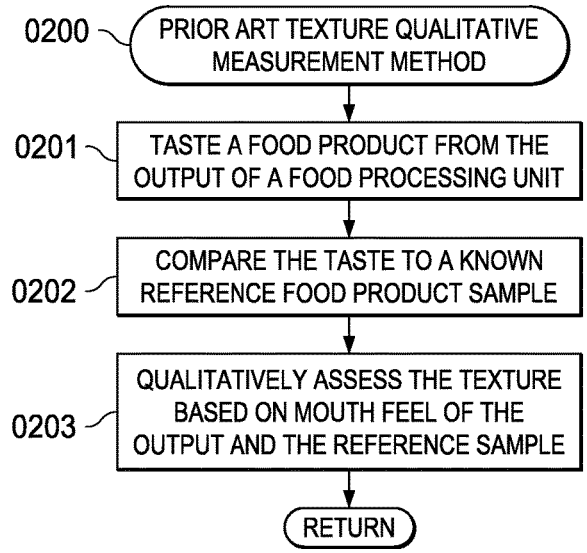
FIG. 2 is a prior art qualitative texture measurement in a manufacturing system.
Figure 3:
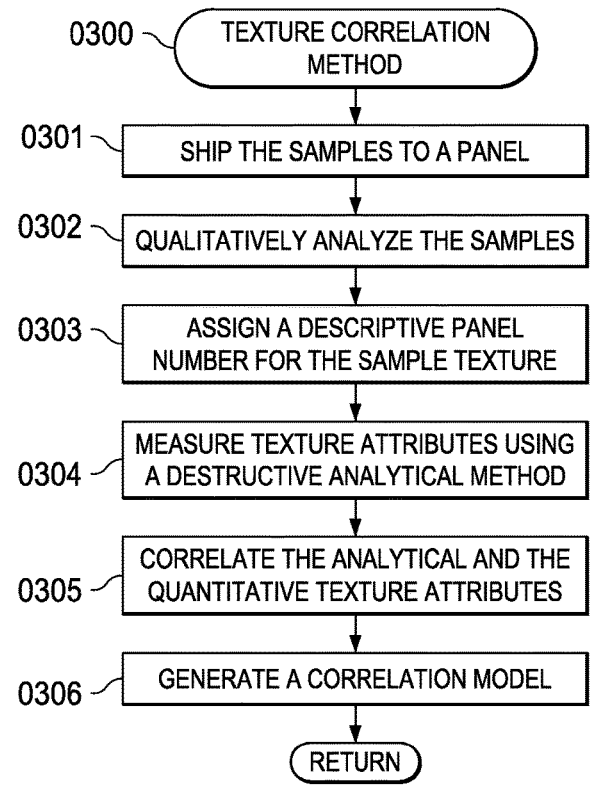
FIG. 3 is a prior art method for correlating texture measurements.

While this invention is susceptible of embodiment in many different forms, there is shown in the drawings and will herein be described in detailed preferred embodiment of the invention with the understanding that the present disclosure is to be considered as an exemplification of the principles of the invention and is not intended to limit the broad aspect of the invention to the embodiment illustrated.

The numerous innovative teachings of the present application will be described with particular reference to the presently exemplary embodiment, wherein these innovative teachings are advantageously applied to quantitative measurement of texture attributes for food snacks apparatus and method. However, it should be understood that this embodiment is only one example of the many advantageous uses of the innovative teachings herein. In general, statements made in the specification of the present application do not necessarily limit any of the various claimed inventions. Moreover, some statements may apply to some inventive features but not to others.

Exemplary Embodiment System for Quantitative Measurement of Texture Attributes (0400)

The term "texture" as used herein is defined a composite property related to a number of physical properties such as hardness, fracturability, tooth-pack, roughness of mass, moistness of mass, residual greasiness, surface roughness, and surface oiliness. It should be noted that the terms "texture" and "texture attribute" is used interchangeably to indicate one or more properties of texture. It should be noted that the term "descriptive panel number", "taste panel score", "qualitative texture number" and "taste panel number" are used inter-changeably to indicate a qualitative measurement of texture measurements by an expert panel. It should be noted that the terms "photo acoustic model" "acoustic model" "acoustic texture model" "quantitative texture attribute model" are used inter-changeably to indicate a quantitative model for a texture attribute of a food snack.

One aspect of the present invention provides a method to quantitatively measure the texture attributes of food snacks. Another aspect of the present invention includes a correlating method between a quantitative texture attribute measurement and a qualitatively measured texture attribute by an expert panel. The present invention is also directed towards developing a texture attribute model based on relevant frequencies in a captured acoustic signal. Another aspect of the present invention includes a closed loop feedback system for continuously controlling texture of a food snack in a manufacturing process. Yet another aspect of the present invention includes a closed loop feedback system and an open loop feed forward system for continuously controlling texture of a food snack in a manufacturing process.

Applicants herein have created an apparatus positioned in a manufacturing system, the apparatus comprises an energy excitation tool for directing energy towards a food snack, an acoustic capturing device for recording/capturing an acoustic signal from the food snack and a data processing unit that processes the captured acoustic signal. In one embodiment, the energy excitation tool is a laser generating tool that is configured to generate a laser. There are a number of embodiments of this invention which fall within the scope of the invention in its broadest sense.

Exemplary Embodiment Texture Measurement Tool (0400)

Figure 4:
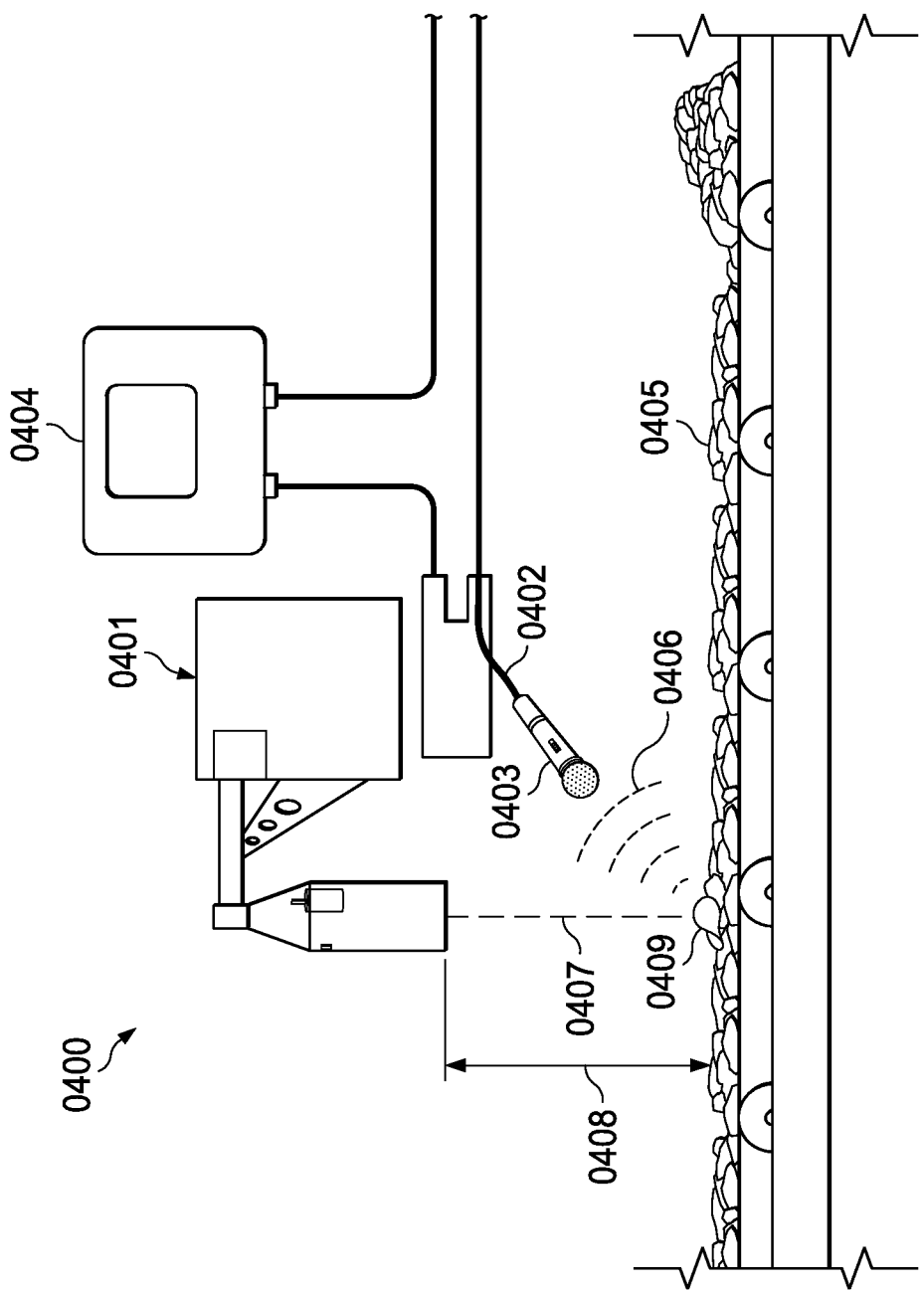
FIG. 4 is a system for quantitative measurement of texture attributes according to an exemplary embodiment of the present invention.

The present invention may be seen in more detail as generally illustrated in FIG. 4, wherein an exemplary texture measurement tool (0400) comprises a housing, an energy excitation tool (0401) that is attached to the housing and positioned to direct electromagnetic wave ("energy") such as a laser (0407) towards a food snack (0409) placed on a food staging station (0405). The food staging station may be a movable or a non-movable surface. According to a preferred exemplary embodiment, the energy excitation tool is a laser generating unit that generates lasers. It should be noted that any tool that can generate excitation on a food substrate may be used as an energy excitation tool. The staging station (0405) may be a flat surface that is used for developing an acoustic model. The staging station (0405) may be a conveyor belt carrying the food snacks when texture is measured in a manufacturing process on-line. According to an exemplary embodiment, an acoustic capturing device (0403) may be positioned to record/capture an acoustic signal (0406) from the food snack (0409). The acoustic capturing device (0403) may be in communication with a data processing unit (DPU) (0404) via a cable (0402) or wirelessly. The acoustic capturing device may capture the acoustic signal across a wide range of frequencies 0 Khz to 500 Khz. Additionally, the acoustic capturing device (0403) may be placed at an angle directly above the food snack (0409). According to a preferred exemplary embodiment, the acoustic capturing device captures acoustic signals in a unidirectional manner. The acoustic capturing device may be in communication with a data processing unit. According to another preferred exemplary embodiment, the acoustic capturing device captures acoustic signals in omnidirectional manner. According to a preferred exemplary embodiment, the acoustic capturing device is a wireless microphone that contains a radio transmitter. In a preferred exemplary embodiment, the acoustic capturing device is a dynamic microphone. In another preferred exemplary embodiment, the acoustic capturing device is a fiber optic microphone. The acoustic capturing device (0403) may be placed at a pre-determined distance and a pre-determined angle from the food snack (0409). The pre-determined distance may be chosen such that it produces optimal acoustics from the food snack. The distance (0408) from the bottom of energy excitation tool (0401) to the top of the staging station (0405) is selected so that the energy beam (laser) is safe within the manufacturing environment.

The acoustic capturing device (0403) may be connected physically with a conducting cable to the DPU (0404) via an input-output module in the DPU (0404). In an alternate arrangement, the acoustic capturing device (0403) may forward an acoustic signal to the input-output module in the DPU (0404) wirelessly. The wireless protocol may use standard protocols such as WIFI or Bluetooth. In an exemplary embodiment, the acoustic capturing device (0403) may be remotely located and the acoustic signal may be forwarded wirelessly to the DPU (0404) with a protocol such as LTE, 3G and/or 4G. In another exemplary embodiment, the remotely located DPU (0404) may be connected to the acoustic capturing device (0403) with wired protocol such as Ethernet.

The energy excitation tool (0401) is positioned to direct energy towards a food snack (0409). It should be noted that the angle of directing as shown is for illustration purposes only. The angle of directing the energy may be configured to produce an optimal excitation of the food snack such that an acoustic capture device (0403) may capture a complete acoustic signal after the excitation tool directs energy towards the food snack. The acoustic signal may then be captured for a period of time. The acoustic signal may be represented as Intensity (dB) vs. Time (secs). According to a preferred exemplary embodiment, the acoustic signal is captured for 1 sec to 5 minutes. According to yet another preferred exemplary embodiment, the acoustic signal from the food snack is captured for 2 sec. According to a more preferred exemplary embodiment, the acoustic signal from the food snack is captured for 1 sec. According to a most preferred exemplary embodiment, the acoustic signal from the food snack is captured for 10 sec.

According to a preferred exemplary embodiment, the energy excitation tool directs energy towards the food snack for a pulse duration or firing time of 5 nanoseconds to 5 minutes. According to yet another preferred exemplary embodiment, the energy excitation tool directs energy towards the food snack for 1 nanosecond. According to a more preferred exemplary embodiment, the energy excitation tool directs energy towards the food snack for 1 minute. According to a most preferred exemplary embodiment, the energy excitation tool directs energy towards the food snack for 9-12 nanoseconds.

Exemplary Energy Excitation Tool (0500)

Figure 5:
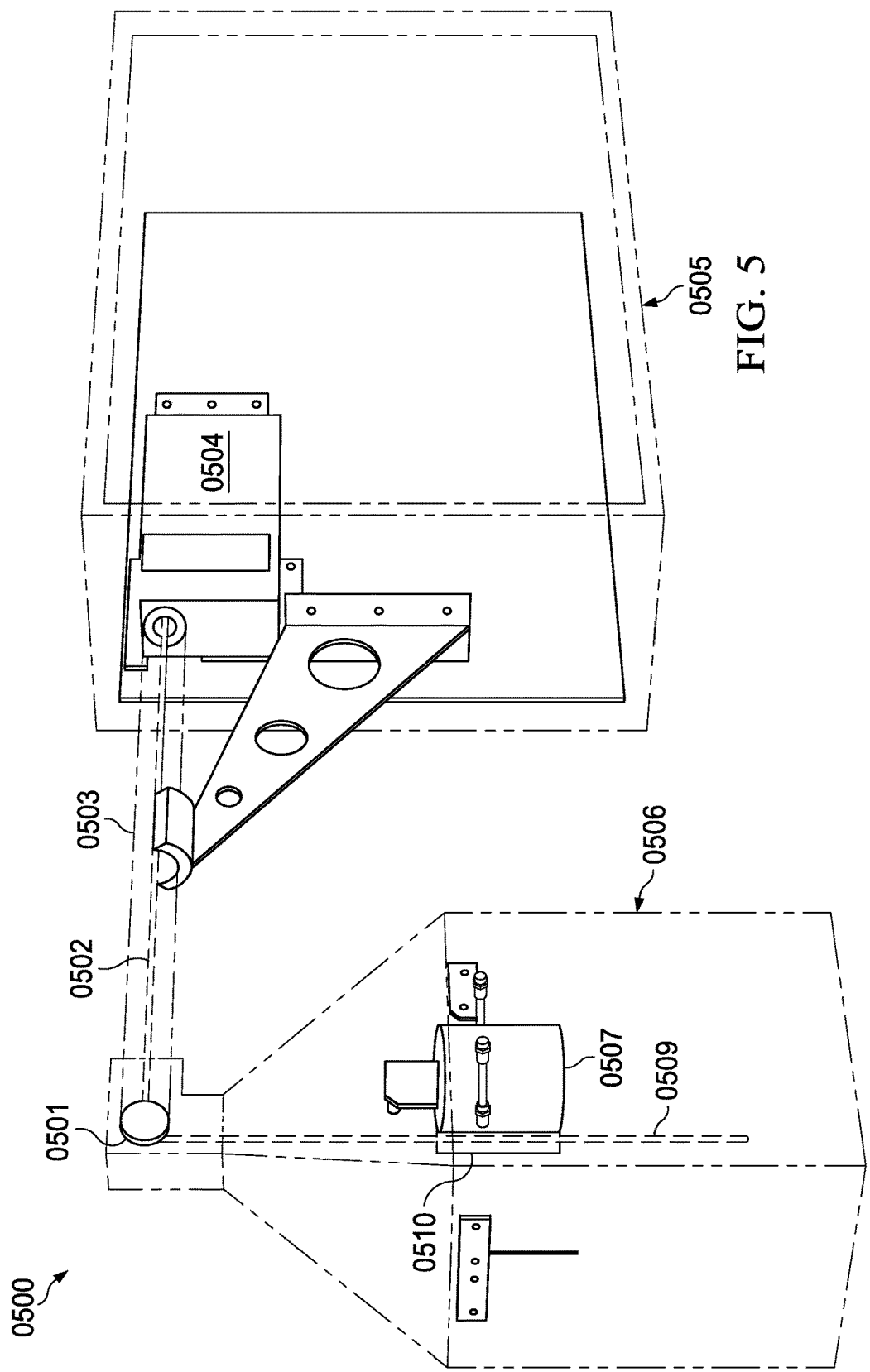
FIG. 5 is an in-line quantitative texture measuring apparatus in a manufacturing system according to an exemplary embodiment of the present invention.

As generally illustrated in FIG. 5 (0500), an exemplary energy excitation tool (0500) that is similar to (0401) in FIG. 4 (0400) comprises an energy generating unit (0504) that is mounted within an energy enclosure (0505). The energy generating unit (0504) may generate an electromagnetic wave that may excite molecules from a food substrate causing the molecules to gain heat energy and vibrate producing a sound. The electromagnetic wave may comprise a wavelength in the range of 512 nm to 2048 nm. A more preferred range of the electromagnetic wave may comprise a wavelength in the range of 470 nm to 1 mm. The energy generating unit (0504) may excite molecules from a food substrate causing the molecules to vibrate a produce sound. Excitation may be defined as an elevation in energy level above an arbitrary baseline energy state. When molecules are excited the thermal expansivity may be related to the type and density of material in accordance with the following equation. Texture may be indirectly related to thermal expansivity and therefore texture is indirectly related to the type and density of the material.

$$\alpha_V = \frac{1}{V}\frac{\partial (V)}{\partial T} = \frac{1}{\frac{1}{\rho}}\frac{\partial\left(\frac{1}{\rho}\right)}{\partial T} = \rho\frac{\partial(\rho^{-1})}{\partial T} = -\frac{\rho}{\rho^2}\frac{\partial(\rho)}{\partial T} = -\frac{1}{\rho}\frac{\partial(\rho)}{\partial T} = -\frac{\partial \ln(\rho)}{\partial T}$$

Thermal expansivity=function (material, density)
Texture=function (material, density)

A specific technical definition for energy level is often associated with an atom being raised to an excited state. The energy excitation tool, in a preferred exemplary embodiment, is a laser generating tool that produces a very narrow, highly concentrated beam of light. A laser is a device that emits light through a process of optical amplification based on the stimulated emission of electromagnetic radiation. Spatial coherence in the laser allows a laser to be focused to a tight spot. Spatial coherence also allows a laser beam to stay narrow over great distances (collimation). Lasers can also have high temporal coherence, which allows them to emit light with a very narrow spectrum, i.e., they can emit a single color of light. The energy generating unit (0504) ("laser generating unit") may include a gain medium, laser pumping energy, high reflector, output coupler and a laser beam. The laser beam (0502) may travel through a hollow tube (0503) and strike a mirror (0501). The hollow tube (0503) may be held by a metallic arm (0512) that is mechanically connected to the energy enclosure (0505). In a preferred exemplary embodiment, the laser beam may travel without the need for a hollow tube. The metallic arm may be made of a metal that may carry the weight of the hollow tube (0503) and the enclosure (0506). The laser may contain additional elements that affect properties of the emitted light, such as the polarization, wavelength, spot size, divergence, and shape of the beam.

The mirror (0501) reflects the laser beam (0502) towards a food snack substrate positioned on a surface. According to a preferred exemplary embodiment, the mirror is angled between 1 degree and 89 degrees to the vertical. According to a most preferred exemplary embodiment, the mirror is angled at 45 degrees to the vertical. Any combination of multiple mirrors, multiple lenses, and expanders may be used to produce a consistent spot size laser that strikes the food snack. The laser beam from the laser generating unit may be redirected, expanded and focused as the beam passes through a combination of mirrors and lenses. It should be noted that even though a single mirror and single lens are illustrated in FIG. 5, it should not be construed as a limitation and any combination of the mirrors, lenses and expanders may be used to produce a constant spot size laser beam. The reflected laser beam (0509) passes through a narrow window (0511) in an enclosure (0506). An acoustic device enclosure (0507) for housing an acoustic capturing device may be mounted in the enclosure (0506). It should be noted that the enclosure (0506) as illustrated in FIG. 5 (0500) is shaped as rectangular, however any shape may be used for the enclosure that is capable of being acoustically insulated and human safe. According to a preferred exemplary embodiment, the enclosure (0506) may be cylindrical, cubical, conical, spherical or triangular prism shaped. Similarly, acoustic device enclosure (0507) may be shaped as rectangular prism, cylindrical, cubical, conical, spherical, or triangular prism. The acoustic device enclosure (0507) may house an acoustic device such as a microphone. The acoustic device enclosure (0507) may also maintain a positive air pressure in order to ensure a particulate free environment within the enclosure (0507). The positive air pressure may be maintained by blowing air through the enclosure with an air pump. According to a preferred exemplary embodiment, the narrow window (0511) may be made out a sapphire material or fused silica. Any translucent window that separates the laser beam from the food product may be used as the narrow window. According to another preferred exemplary embodiment, the narrow window (0511) is aligned such that the laser beam (0509) is within +−1 degrees to a desired direction. The desired direction may be vertical or at an angle to a vertical plane. A laser level sensor (0510) is positioned within the enclosure (0506) to sense the level of the food from the surface. The laser sensor (0501) may prevent humans from undesired entry into the enclosure (0506). For example, if the laser sensor detects an object or a human hand over the food snack, it may automatically shut off the laser and prevent from exposing the human to the laser. According to a preferred exemplary embodiment, the laser level provides for a human safe laser environment. According to another preferred exemplary embodiment, the laser level detects a food snack within +−2 inches from a staging surface.

Exemplary Data Processing Unit (0600)

Figure 6:
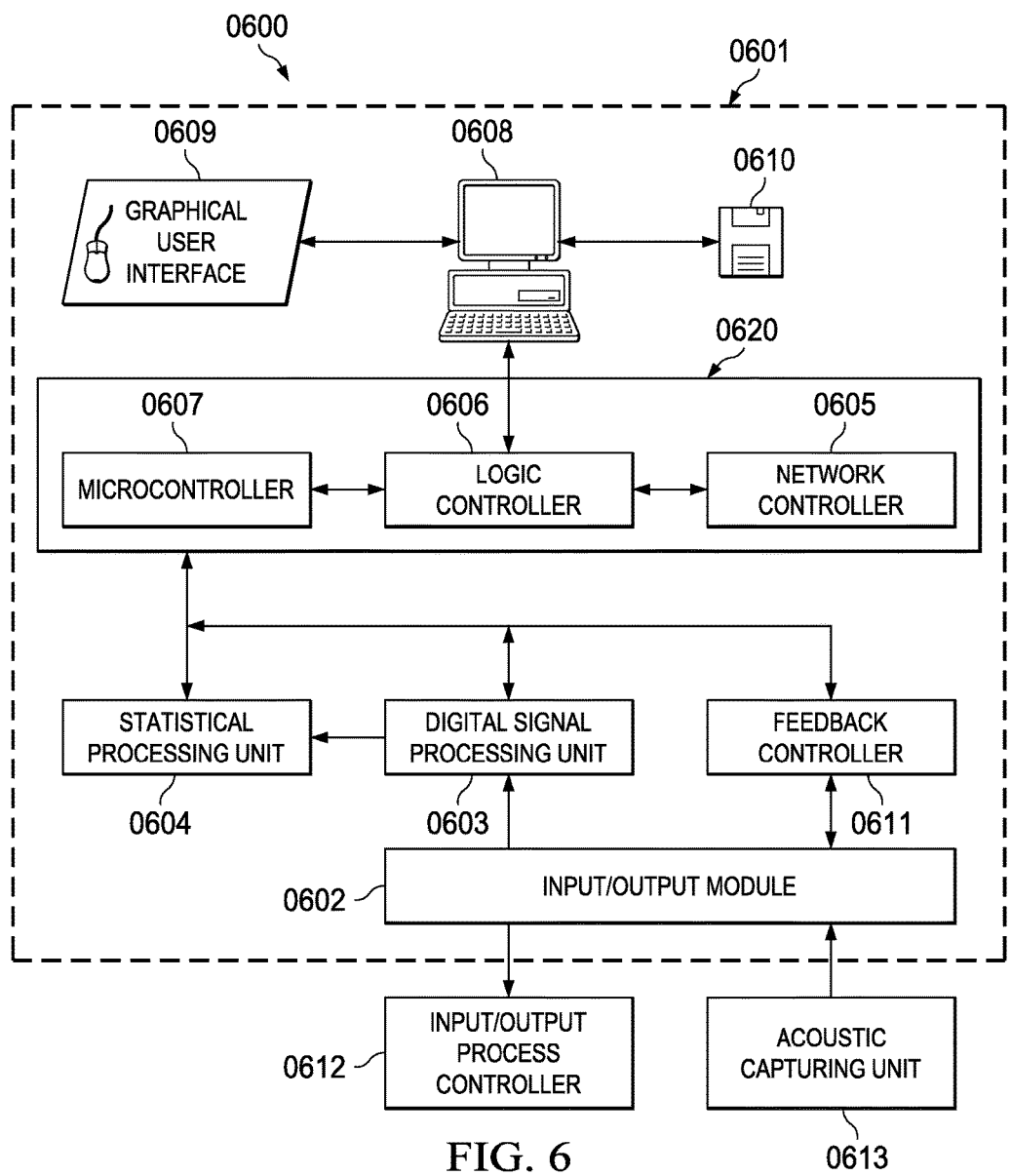
FIG. 6 is a data processing unit according to an exemplary embodiment of the present invention.

As generally illustrated in FIG. 6 (0600), a data processing unit (DPU) (0601) comprises a control unit (0620), a display unit, a processing unit and an input output module (0602). The control unit may further comprise a microcontroller (0607), a logic controller (0606), and a network controller (0605). The display unit may be connected to the control unit via a host bus. The display unit may further comprise a display terminal (0608) that is configured to display a graphical user interface (GUI) (0609). The GUI (0609) may be navigated with a pointing device or through a keyboard connected to the DPU. The GUI (0609) may be used to input parameters such as food snack specific frequencies, acoustic capture time, acoustic capture frequency range, mirror tilt, laser sensor level, laser window opening.

The processing unit may include a digital signal processing unit (0603) and a statistical processing unit (0604). The digital signal processing unit (0603) may receive input from an input-output module (0602). The statistical processing unit (0604) may receive input from the digital processing unit (0603) and further process the input to identify relevant frequencies for generating a quantitative model for a food snack. When an acoustic capturing device captures an acoustic signal, the signal may be forwarded to the DPU (0601) via the input-output module (0602). The acoustic signal may be forwarded to the DPU (0601) with a wired or a wireless connection. The connection protocol and connecting conducting wires may be chosen such that there is minimum loss of signal and the signal to noise ratio is acceptable for further processing. A general purpose bus may carry data to and from different modules of the DPU. It should be noted that the operation of the bus is beyond the scope of this invention.

The microcontroller (0607) may perform instructions from a memory or a ROM (0610). The instruction set of the microcontroller may be implemented to process the data of the acoustic signal. A custom instruction set may also be used by the microcontroller to prioritize and expedite the processing of the acoustic signal in real time during a manufacturing operation. The customization of the instruction set is beyond the scope of this invention. The logic controller may perform operations such as sequencing, prioritization and automation of tasks. The logic controller may also oversee the hand shake protocol for the bus interface. According to an exemplary embodiment, the logic controller controls the logic for identifying relevant frequencies in an acoustic signal. The logic controller may comprise a matching module that contains predefined frequencies for a plurality of food snacks. The logic controller may subsequently match the captured frequencies in the acoustic signal and quickly determine the texture of the food snack and the quality of the texture. For example, the matching module may include specific frequencies such as 14000 Hz and 75000 Hz. When a recorded acoustic signal comprises the frequencies 14000 Hz or 75000 Hz, then the logic controller may determine a match and alert the microcontroller with an interrupt signal. The microcontroller may then display the texture information on the display (0608) via GUI (0609). The logic controller may further continuously monitor the state of input devices and make decisions based upon a custom program to control the state of output devices.

According to an exemplary embodiment, a feedback controller controls an input/output controller to adjust parameters to food processing modules such that the resultant output properties of the food snacks from the food processing modules fall within an acceptable range. As generally illustrated in FIG. 6 (0600), during a manufacturing process, food snack conveyed on a belt are struck with an excitation energy from an excitation tool. The resulting acoustic signal may be captured by an acoustic capturing unit (0613) and forwarded to the input/output module (0602). The input/output module (0602) may further forward the acoustic signal to the digital signal processing unit (DSP) (0603) which processes the acoustic signal.

The DSP (0603) may further comprise a smoothing module, a data transformation module, a signal to noise enhancing module and a normalization module.

According to a preferred exemplary embodiment, the acoustic smoothing module receives input from an input-output module (0602) in a data processing unit and smoothens the received raw acoustic signal. Acoustic signals are inherently noisy and the data is discrete. The acoustic signals may be represented as Intensity (dB) vs. Time (secs). The data is made continuous by applying a windowing function to the discrete data. Windowing functions that may be applied to the discrete data may include Barlett, Blackmon, FlatTop, Hanning, Hamming, Kaiser-Bessel, Turkey and Welch windowing functions. A smoothing window with good frequency resolution and low spectral leakage for a random signal type may be chosen to smoothen the data. It should be noted that any commonly known windowing function may be applied to a raw acoustic signal to smoothen and interpolate the raw acoustic data.

The smoothened acoustic signal from the smoothing module may be forwarded to a data transformation module. The data transformation module may transform the acoustic signal represented in time domain as Intensity (dB) vs. Time (secs) to frequency domain as Intensity (dB) vs. Frequency (Hz). According to a preferred exemplary embodiment, the transformation of acoustic signal from a time domain representation to a frequency domain representation provides for accurately correlating texture attributes to the pertinent frequencies of a food snack. Combining multiple acoustic waves produces a complex pattern in the time domain, but the transformed signal using FFT clearly shows as consisting almost entirely of distinct frequencies. According to most preferred exemplary embodiment, a fast fourier transformation (FFT) technique may be used to transform the acoustic signal from a time domain representation to a frequency domain representation. An example of the transformation may be generally seen in FIG. 10 (1000).

The transformed frequency signal from the transformation module may be noisy. A signal to noise enhancement module may receive the transformed signal from the data transform module and enhance the signal-to-noise ratio of the signal for further processing. A technique for smoothing the data to increase the signal-to-noise ratio without greatly distorting the signal may be used. A process such as convolution may also be used to increase the signal-to-noise ratio. The convolution process may fit successive sub-sets of adjacent data points with a low-degree polynomial by the method of linear least squares. A normalization module may receive the enhanced signal-to-noise frequency domain signal from the signal to noise enhancement module.

The identified frequencies and the associated intensities are recorded for each normalized acoustic signal. A model for each attribute of a food snack may be input into the DPU (0601). The model for the attribute may be developed with a method as described in FIG. 9 (0900). The identified frequencies and the associated intensities are then substituted into the model to determine an attribute for the food snack. The micro controller (0607) may then direct a signal to instruct the feedback controller (0611) so that a controller to the units of a food processing unit or food pre-processing unit adjusts input parameters of the food processing unit or food pre-processing unit. Depending on the instructions from the microcontroller (0607), the feedback controller (0611) may communicate with an input/output process controller (0612). The input/output process controller (IOC) (0612) may be a conventional process control device such as PI, PID or a PD controller. Advanced process control techniques such as predictive controls techniques, fuzzy logic, inferential techniques, constant model predictive control (CMPC), multiple input multiple output (MIMO), single input multiple output (SIMO), single input single output (SISO), and supervisory control element that ultimately provides a set point may be used in conjunction with the IOC (0612). The IOC (0612) may adjust the input parameters such as input temperature, dwell time to food processing units such as a fryer. The IOC (0612) may also adjust the input parameters such as slice thickness to food pre-processing units such as a food slicer.

A statistical processing unit (SPU) (0604) shown in FIG. 6 (0600) may further comprise a dimensionality regression module, a variance inflation factor module, a principal component analysis module, and a subset regression module. The smoothened, transformed and normalized signal from the digital signal processing unit (0603) is forwarded to SPU (0604) for developing texture attribute model with good correlation. An $R^2$ value greater than 0.9 may be considered a good correlation between the measure value from the model and descriptive expert panel number.

Exemplary Texture Attribute Measurement Method

Figure 7:
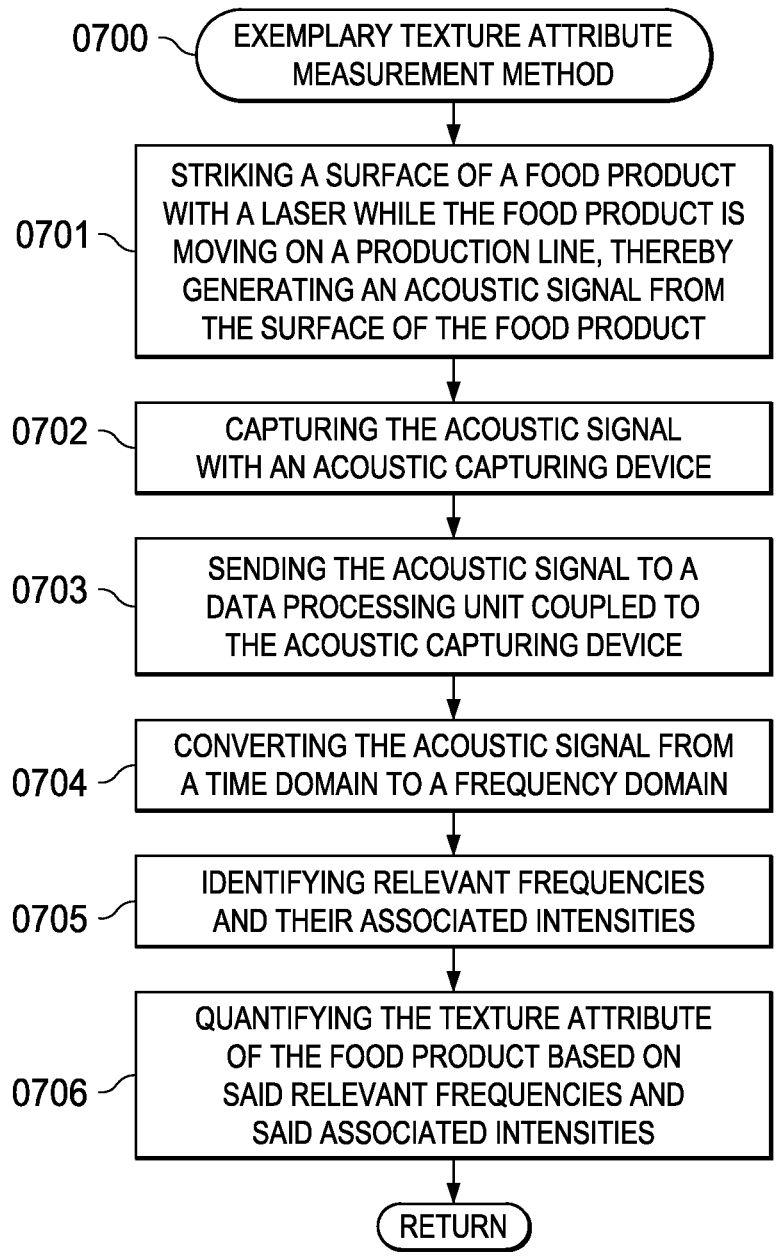
FIG. 7 is a flow chart method for quantitative measurement of texture according to an exemplary embodiment of the present invention.

As generally shown in FIG. 7, an exemplary texture measurement method may be generally described in terms of the following steps:
(1) striking a surface of a food product with a laser while the food product is moving on a production line, thereby generating an acoustic signal from the surface of the food product (0701);
(2) capturing the acoustic signal with an acoustic capturing device (0702);
(3) sending the acoustic signal to a data processing unit coupled to the acoustic capturing device (0703);
(4) converting the acoustic signal from a time domain to a frequency domain (0704);
 acoustic signal is captured for a period of time and the signal is plotted as Intensity (dB) vs. time (seconds)
(5) identifying relevant frequencies and their associated intensities (0705); and
(6) quantifying the texture attribute of the food product based on said relevant frequencies and said associated intensities (0706).
 Substitute the relevant frequencies and associated intensities in the acoustic signal from step (6) into an acoustic model and compute the texture attribute.

This general method summary may be augmented by the various elements described herein to produce a wide variety of invention embodiments consistent with this overall design description.

Exemplary Texture Attribute Correlation Method

Figure 8:
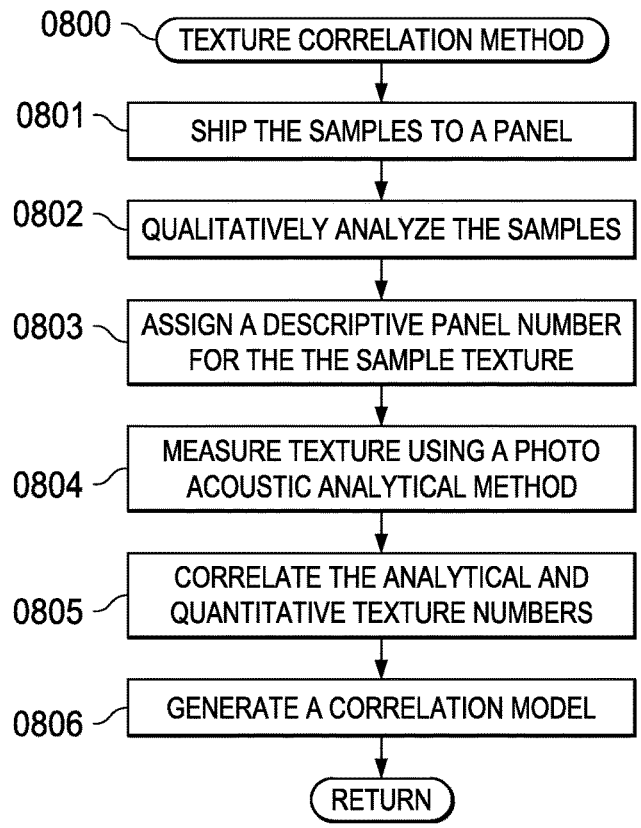
FIG. 8 is an exemplary flow chart method for quantitative correlation of texture according to a preferred embodiment of the present invention.

As generally shown in FIG. 8, an exemplary texture correlation method may be generally described in terms of the following steps:
(1) shipping food snack samples to an expert panel (0801);
 The shipping of the food snack samples may take time and the food snack may undergo texture change during the shipping process. The number of times samples are shipped to an expert panel is substantially reduced due a high correlation quantitative model developed according to a preferred exemplary embodiment.
(2) Qualitatively analyzing the food snack samples (0802);
 quantitatively measure texture attributes by an expert panel for assigning taste panel scores.
(3) Assigning a descriptive panel number for the texture attributes of the food snack sample (0803);
(4) Measuring texture attributes with an quantitative texture model (0804);
(5) Correlating the quantitative texture attributes and the qualitative expert panel texture attributes (0805); and
(6) Generating a correlation for the texture attributes (0806).
 The $R^2$ of the correlation is targeted to be greater than 0.9.

This general method summary may be augmented by the various elements described herein to produce a wide variety of invention embodiments consistent with this overall design description.

Exemplary Texture Attribute Model Development Method

Figure 9:
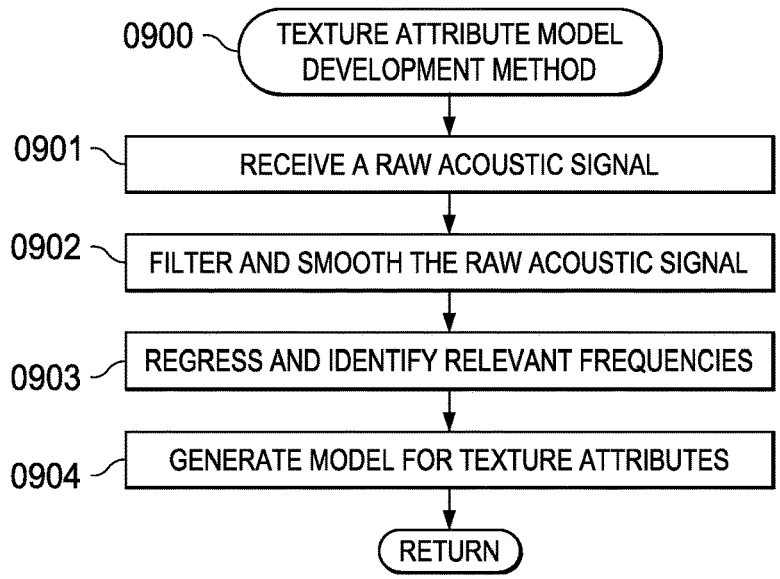
FIG. 9 is an exemplary flow chart method for quantitative texture model development according to a preferred embodiment of the present invention.

As generally shown in FIG. 9, an exemplary texture attribute model development method may be generally described in terms of the following steps:
(1) Receiving a raw acoustic signal (0901);
(2) Filtering, smoothing and transforming the raw acoustic signal (0902);
(3) Regressing and identifying relevant frequencies (0903);
(4) Generating a model for the texture attributes (0904).

This general method summary may be augmented by the various elements described herein to produce a wide variety of invention embodiments consistent with this overall design description.

Exemplary Acoustic Signal Time Domain to Frequency Domain Conversion (1000)

Figure 10:
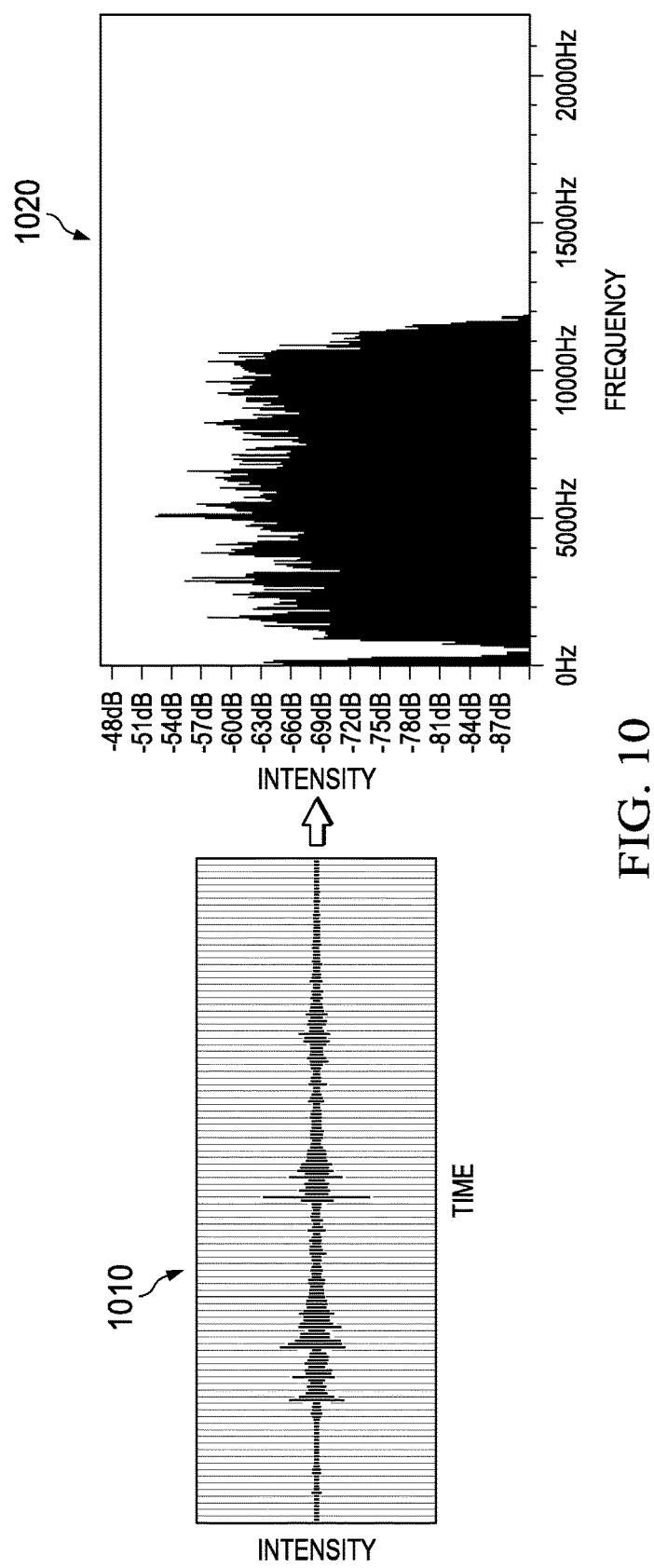
FIG. 10 is an exemplary acoustic signal time domain to frequency domain transformation chart according to a preferred embodiment of the present invention.

As generally illustrated in FIG. 10, an exemplary acoustic signal captured in time domain (transient) (1010) is converted to a frequency domain (1020) with Fourier transformation. When a laser strikes a food snack, an acoustic signal is captured in time domain and is recorded and plotted as Intensity (dB) vs. time (secs). The recorded acoustic signal may be transformed into a frequency domain signal as illustrated in FIG. 10 (1020). The transformed acoustic signal may be further processed to identify relevant frequencies based on a statistical regression analysis. An acoustic model to quantitatively measure a texture attribute may be developed with the identified relevant frequencies and their associated intensities as variables as described in equation (1).

Exemplary Texture Attribute vs. Relevant Frequencies Chart (1100-1200)

Figure 11:
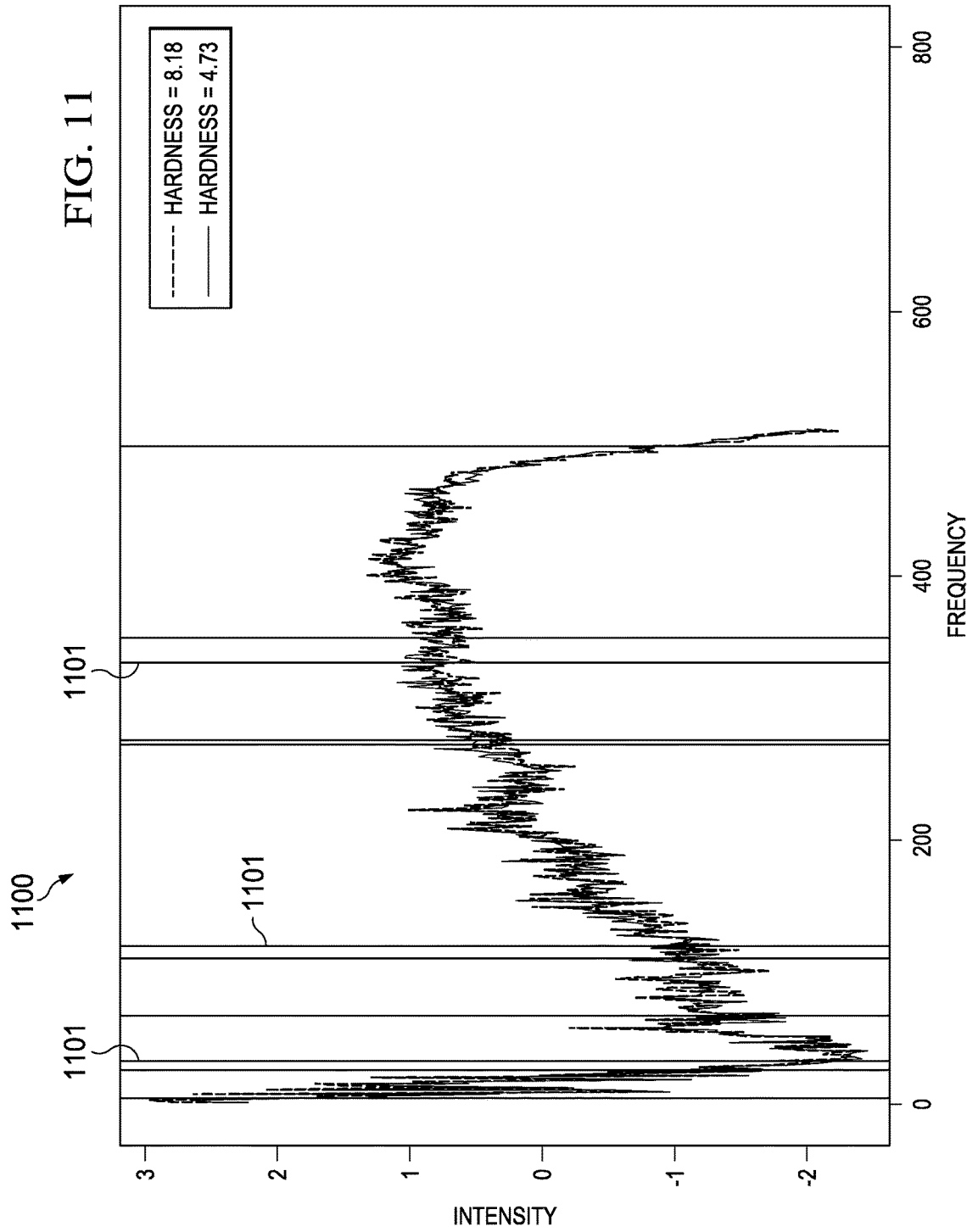
FIG. 11 is an exemplary texture attribute (hardness) vs. relevant frequencies chart according to a preferred embodiment of the present invention.
Figure 12:
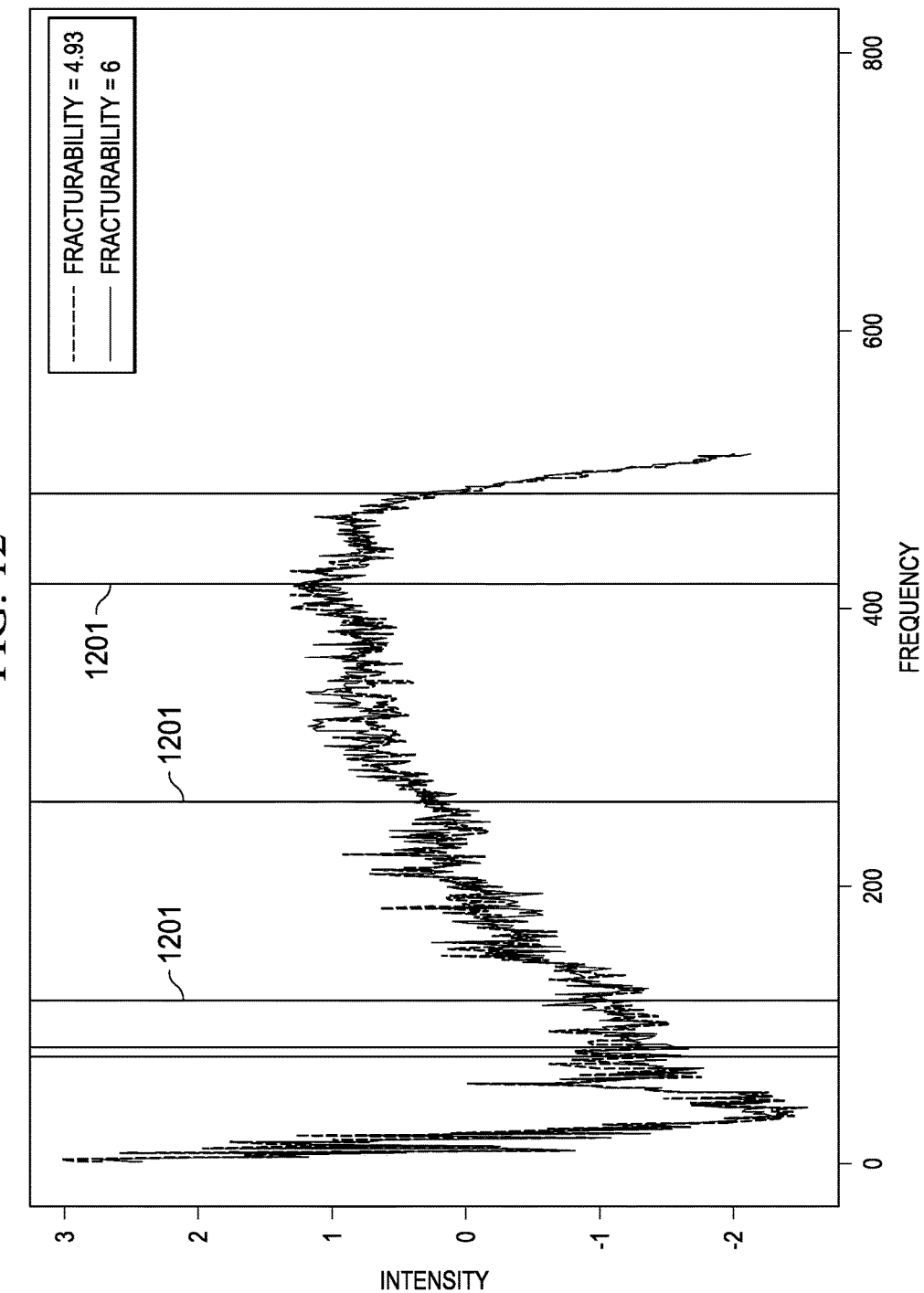
FIG. 12 is an exemplary texture attribute (fracturability) vs. relevant frequencies chart according to a preferred embodiment of the present invention.

As generally illustrated in FIG. 10 and FIG. 11, an exemplary texture attribute vs. relevant frequencies chart may be used to compute the hardness of a food snack. The relevant frequencies may be identified by a statistical regression for a particular texture attribute and a food snack. For example, frequencies (1101) may be relevant for hardness and frequencies (1201) may be relevant for fracturability as determined by a statistical analysis described in FIG. 9 (0900). According to a preferred exemplary embodiment, the relevant frequencies and corresponding intensities identified in a transformed acoustic signal may be substituted in an acoustic model to quantitatively measure a texture attribute such as hardness. It should be noted that the frequencies indicated on x-axis are frequency "buckets" as determined by an algorithm, and not the literal frequencies (i.e. 400 may not be 400 Hz, but mapped to 18,000 hz).

Exemplary Food Snack Manufacturing System Embodiment (1300)

Figure 13:
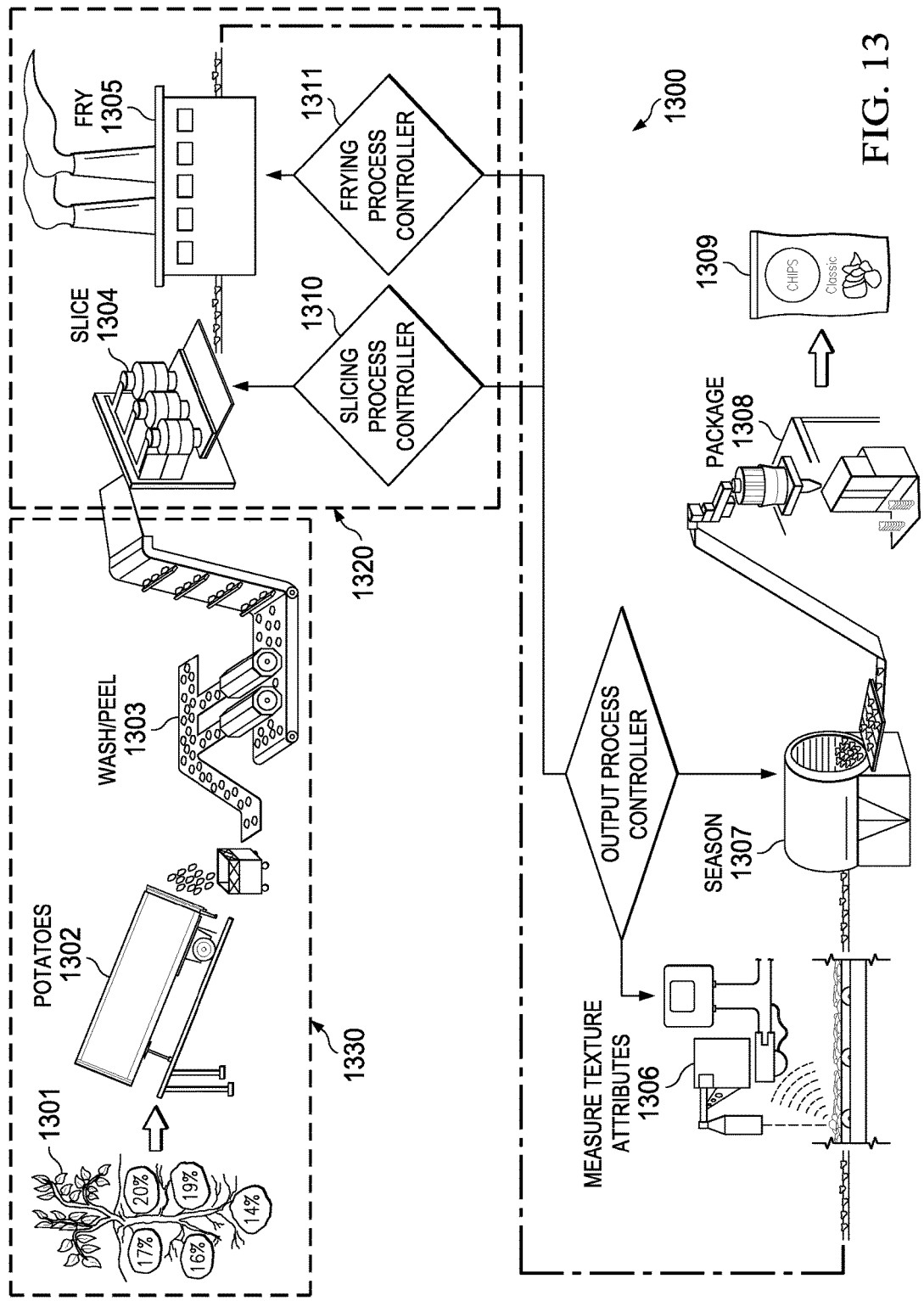
FIG. 13 is an exemplary quantitative texture feedback manufacturing system according to a preferred embodiment of the present invention.

As generally illustrated in FIG. 13 (1300), an exemplary food snack manufacturing system comprises an acoustic quantitative texture measurement tool (1306) that is positioned after a food processing unit (FPU) (1320). The system (1300) illustrated in FIG. 13 (1300) may be used to manufacture potato chips and other food snacks. The manufacturing system may comprise a series of inter connected stations that include a sourcing stage (1301), a storage station (1302), wash/peel station (1303), slicing station (1304), frying station (1305), measurement station (1306), a seasoning station (1307), a packaging station (1308) and a labeling station (1309). The food snacks, such as potato chips, may be conveyed from station to station on a conveyor belt in the manufacturing system. The storage station (1302) and the wash/peel station may be combined as a preprocessing unit (1330). The FPU (1320) may include one or more of the processing units such as slicing station (1304) and frying station (1305). The slicing station (1304) may be connected to a slicing process controller (1313) that controls input parameters to the slicing station (1304) such as slicing thickness, moisture control, and slicing ridges. The frying station (1305) may be connected to a fryer process controller (1311) that controls input parameters to the frying station (1305) such as oil input temperature, oil output temperature, oil volume, and frying dwell time. According to a preferred exemplary embodiment, an in-line feedback control with acoustic quantitative texture measurement tool enables a consistent manufacturing food texture quality. According to a preferred exemplary embodiment, the acoustic quantitative texture measurement tool (1306) may be positioned immediately after the FPU (1320) and before a seasoning unit (1307) or packaging unit (1308). The texture measurement tool (1306) may be placed between any two stations in the process to capture acoustic signals from the passing product after laser excitation. According to a preferred exemplary embodiment, the tool (1306) records/captures acoustic signal when an energy excitation tool strikes the food snack from FPU (1320) and processes the acoustic signal to quantitatively measure a texture attribute with an acoustic model. The energy excitation tool may strike the food snack and produce an acoustic signal as described below.

Exemplary Photo Acoustic Signal Method (1) Creating small region of highly-heated material in a food product;
(2) Expanding the material rapidly;
(3) Creating pressure waves from the material;
(4) Propagating the pressure waves through the air as sound.

The acoustic model may be developed using the method described in FIG. 9 (0900). The model may be programmed into the tool (1306) for measuring one or more texture attributes such as hardness, fracturability and denseness. An acoustic model for texture attribute hardness may be described below:

Hardness=$f(X_{1-n}, I_{1-n})$

Hardness=$I_1 C_1 + I_2 C_2 + I_3 C_3 + \ldots I_n C_n$ (1)

Where, $I_n$ is an intensity associated with a frequency $X_n$
$C_n$ is a coefficient associated with the frequency $X_n$
Coefficients ($C_1$-Cn) are determined using the energy excitation method described in FIG. 9 (0900). A signal processing unit in the texture measurement tool (1306) identifies the relevant frequencies ($X_n$) and associated intensities ($I_n$). The tool (1306) may calculate a texture attribute such as hardness from the above model 1 by substituting the coefficients values ($C_1$-Cn) from a stored table for the food snack and the intensities ($I_n$) from the processed acoustic signal. Similarly, other texture attribute such as fracturability and denseness may be calculated from their respective models comprising the respective coefficients. It should be noted that even though the above represented model (1) shows a linear relationship between the texture attribute and intensities, a quadratic or polynomial model may also be represented to calculate the texture attributes.

Similar acoustic models may be developed for models for other food properties such a moisture, solids content, oil content, slice thickness, density, blister density and topical seasonings. The relevant frequencies and associated intensities and the coefficients of the developed model may change depending on the food property. A generic model that may represent a food property may be described below:

Food property=$f(Z_{1-n}, P_{1-n})$

Food Property=$P_1 D_1 + P_2 D_2 + P_3 D_3 + \ldots P_n D_n$ (2)

Where, $I_n$ is an intensity associated with a frequency $X_n$
$C_n$ is a coefficient associated with the frequency $X_n$
Coefficients ($D_1$-Dn) are determined using the energy excitation method described in FIG. 9 (0900). A signal processing unit in the texture measurement tool (1306) identifies the relevant frequencies ($Z_n$) and associated intensities ($P_n$). In addition to texture attribute, the tool (1306) may calculate a food property from the above model (2) by substituting the coefficients values ($D_1$-Dn) from a stored table for the food snack and the intensities ($P_n$) from the processed acoustic signal. The food properties may include Solids content, Moisture, Density, Oil content, Slice thickness, Seasoning particle size, and elements such as sodium, calcium, copper, zinc, magnesium, and potassium.

It should be noted that even though the above represented model (1) shows a linear relationship between the texture attribute and intensities, a quadratic or polynomial model may also be represented to calculate the texture attributes. The food property may also be compensated for changes in temperature of the food snack and the distance of the food snack from the focal point of the laser beam. A table 1.0 may be used to measure food properties as shown below from a captured and processed acoustic signal. The values shown below in table 1.0 are for illustration purposes only and should not be construed as a limitation.

TABLE 1.0

| Food Property | Relevant Frequencies ($Z_n$) | Intensities ($P_n$) | Coefficients ($D_n$) | Value | Limits |
|---|---|---|---|---|---|
| Texture Attribute | 14000 Hz | 68 | 3.5 | 7 | 4 to 10 |
| | 15000 Hz | 71 | 2.3 | | |
| Solids content | 16000 Hz | 75 | 1.1 | 17 | 12 to 25 |
| | 33,000 Hz | 77 | 9.0 | | |
| Density | 88000 Hz | 83 | 8.2 | 1.3 | 1 to 12 |
| Oil content | 16000 Hz | 59 | 2.5 | 36% | 20% to 46% |
| | 49,000 Hz | 70 | 2.9 | | |
| Slice thickness | 76000 Hz | 64 | 4.3 | 0.055 | 0.035 to 0.075 |
| Seasoning particle size | 64000 Hz | 74 | 8.8 | 0.5% | 0.1% to 15% |
| Element | 97000 Hz | 82 | 3.7 | Na (sodium) | Can be any listed element |

As the food products such as food snacks, on a conveyor belt pass from the FPU (1320) to the seasoning station (1307), the excitation tool in the measurement tool (1306) may strike the food snack repeatedly for a set period of time. The food product may be moving when a laser strikes the food product. The food product may be stationary momentarily while the laser strikes the food product. According to a preferred exemplary embodiment, the excitation tool may continuously strike the food snack for a period of 1 micro second. According to a yet another preferred exemplary embodiment, the excitation tool may continuously strike the food snack for a period of 1 second. According to a more preferred exemplary embodiment, the excitation tool may continuously strike the food snack for a period of 1 second to 10 seconds. According to a most preferred exemplary embodiment, the excitation tool may continuously strike the food snack for a period of 13 seconds. The excitation tool may strike a particular food snack on the conveyor belt repeatedly so that multiple acoustic signals are generated for the entire surface of the food snack. It is known that the texture attribute may not be uniform across the entire surface. The excitation energy may strike the food snack across the entire area of the food snack so that any imperfections such as blisters may be detected after the signal has been processed. According to a preferred exemplary embodiment, repeatable measurements for a period of time, enables the measurement tool to identify subtle variations across the entire surface of a food snack. The signal may be captured/recorded by an acoustic capturing device in the texture measurement tool (1306).

The acoustic capturing device may capture the acoustic signal across a wide range of frequencies. Additionally, the acoustic capturing device may be placed at an angle directly above the food product. According to a preferred exemplary embodiment, the acoustic capturing device captures acoustic signals in a unidirectional manner. According to another preferred exemplary embodiment, the acoustic capturing device captures acoustic signals in omnidirectional manner. The acoustic capturing device may forward the captured acoustic signal to a processing device physically through a cable. According to a preferred exemplary embodiment, the acoustic capturing device is a wireless microphone that contains a radio transmitter. In a preferred exemplary embodiment, the acoustic capturing device is a dynamic microphone. In another preferred exemplary embodiment, the acoustic capturing device is a fiber optic microphone. A fiber optic microphone converts acoustic waves into electrical signals by sensing changes in light intensity, instead of sensing changes in capacitance or magnetic fields as with conventional microphones. The acoustic capturing device may use electromagnetic induction (dynamic microphones), capacitance change (condenser microphones) or piezoelectricity (piezoelectric microphones) to produce an electrical signal from air pressure variations. The microphones may be connected to a preamplifier before the signal can be amplified with an audio power amplifier or recorded. The microphones may be regularly calibrated due to the sensitivity of the measurement. In another preferred exemplary embodiment, the acoustic capturing device has a digital interface that directly outputs a digital audio stream through an XLR or XLD male connector. The digital audio stream may be processed further without significant signal loss. According to a preferred exemplary embodiment the acoustic capturing device may be a hydrophone. The hydrophone may be in communication with a data processing unit. The hydrophone may be used in fluid environments.

According to a preferred exemplary embodiment, depending on the measured texture attribute, an output controller (1312) may control the output quality from the FPU (1320). The output controller (1312) may be connected to a slicing input controller (1313) and a frying input controller (1311). Typical process control equipment such as PI, PID control devices, may be used to control the input parameters of the slicing station (1304) and frying station (1305). For example, if the texture attribute, hardness, falls outside an acceptable limit, the output controller (1312) may adjust an input parameter to the frying unit such as frying temperature or frying time. The output controller (1312) may adjust an input parameter to the slicing unit so that the slices are thinner or thicker depending on the correlation of the output texture attribute to the input parameters. According to a preferred exemplary embodiment, the texture measuring tool (1306) continuously feeds back information to control input parameters to the food processing unit (1320) such that the texture attribute of the food product falls within an acceptable limit. The acceptable limit may be determined by correlating the acoustic model and a descriptive panel number. A tighter acceptable limit may indicate a more controlled quality process. The acceptable limit may also be further tuned as more data is collected. Each texture attribute may have its own acceptable limits. The measured texture attributes may be monitored continuously and charted for sustaining process quality control.

Exemplary Food Product Manufacturing Method Embodiment (1400)

Figure 14:
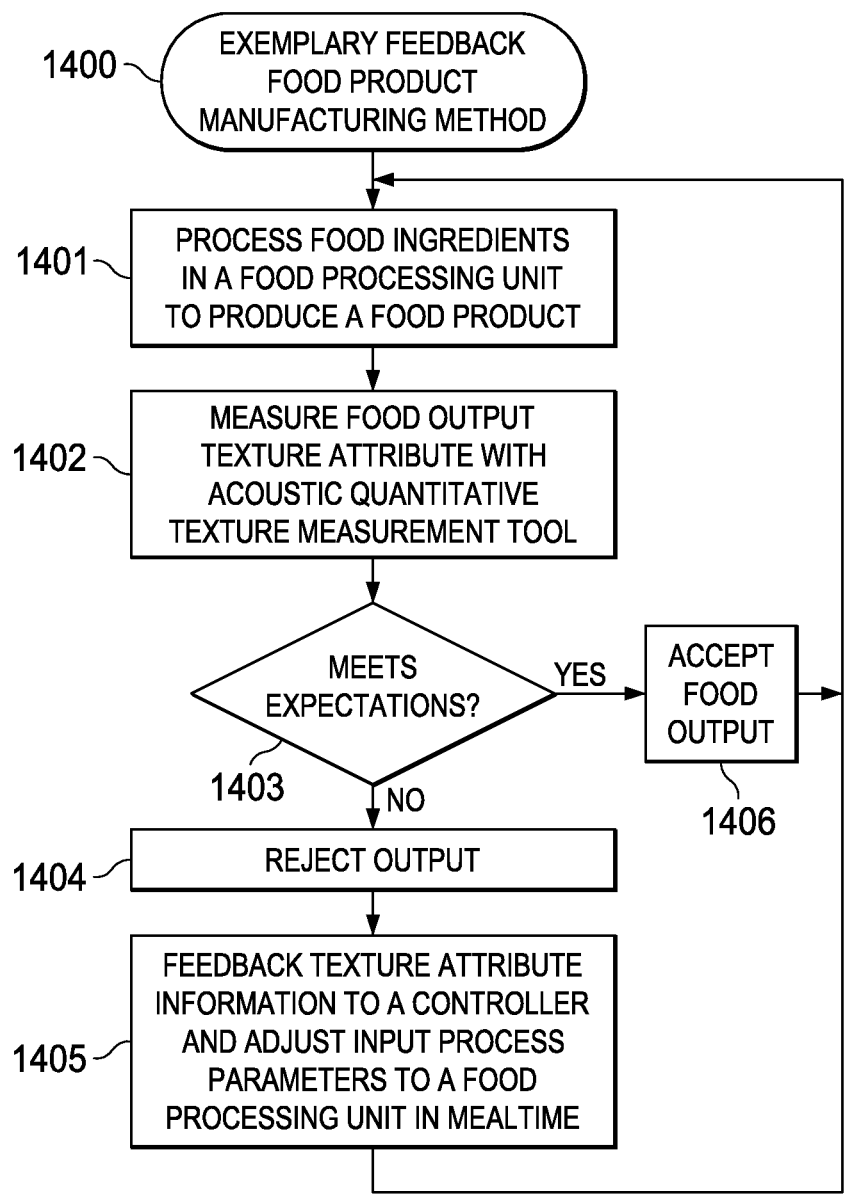
FIG. 14 is an exemplary quantitative texture feedback manufacturing method according to a preferred embodiment of the present invention.

As generally shown in FIG. 14, a an exemplary feedback manufacturing method associated with the feedback manufacturing system in FIG. 13 may include the steps comprising:

(1) processing food ingredients in a food processing unit to produce the food product (1401);

The food product may be a food snack such as potato chips. The food product may be any starch based food snack.

(2) measuring a texture attribute of the food product with a texture measuring tool (1402);

each of the texture attributes such as hardness, fracturability, tooth-pack, roughness of mass, moistness of mass, residual greasiness, surface roughness, and surface oiliness may be measured in this step. Food properties such as moisture, solids content, oil content, slice thickness, density of solids, topicals, seasonings such as sodium chloride and any flavors/seasonings with particle sizes between 100 microns and 500 microns may be measured in addition to the texture attribute. The food product may be moving when a laser strikes the food product. The food product may be stationary momentarily while the laser strikes the food product.

(3) determining if each of the texture attribute is within an acceptable limit, if so, proceeding to step (1406) (1403);

(4) if the texture attribute is outside an acceptable limit in step (1103), rejecting the food product (1404);

(5) feeding back texture attribute information to a controller to adjust input parameters to the food processing unit, proceeding to step (1401) (1405); and (6) accepting the food product and proceeding to step (1401) (1406).

This general method summary may be augmented by the various elements described herein to produce a wide variety of invention embodiments consistent with this overall design description.

Exemplary Texture Attribute vs. Input Parameter Correlation Chart (1500-1600)

Figure 15:
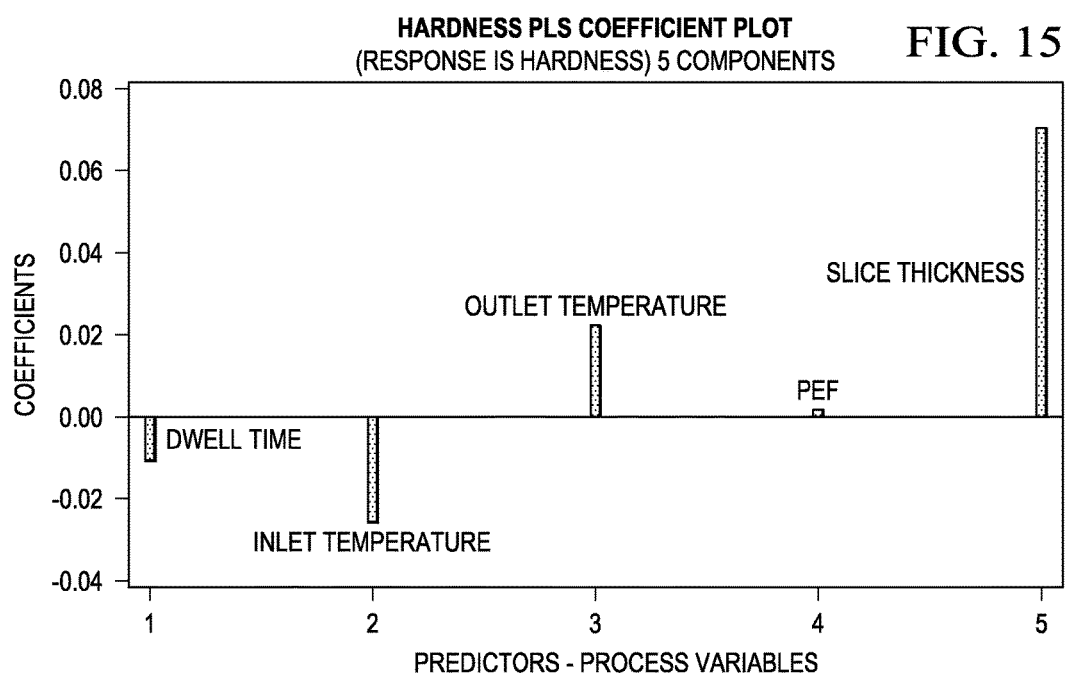
FIG. 15 is an exemplary texture attribute (hardness) vs. Input parameter correlation chart according to a preferred embodiment of the present invention.

FIG. 15 generally illustrates an exemplary texture attribute (hardness) vs. Input parameter correlation chart. The x-axis is an input parameter such as inlet temperature, outlet temperature, dwell time, and slice thickness. The y-axis is a correlation coefficient that may be utilized to adjust the input parameters to a controller controlling a food processing unit. The correlation between a quantitative output texture attribute and the input parameters may be developed through statistical models and experimentation. After a model has been developed, an output texture attribute may be measured and depending on the measurement, the input parameters may be controlled through a feedback controller (0611) and input/output controllers (0612) as aforementioned in FIG. 6 (0600). The correlation model between a quantitative output texture attribute and the input parameters may be an equation (2) as described below $$\text{Hardness} = P_1 A_1 + P_2 A_2 + P_3 A_3 + \ldots P_n A_n \quad (3)$$

Where, $P_n$ is an input parameter $A_n$ is a coefficient associated with the Input parameter $P_n$ (The Coefficients may be positive or negative depending on the direction of correlation).

In a general example, if the hardness of a food product is higher than an acceptable limit as measured by a quantitative texture measurement tool positioned in a manufacturing line, then the slice thickness may be decrease or the dwell time may be decreased. As seen in FIG. 15 (1500), the hardness of a food product may be controlled by adjusting one or more of the input parameters ("process variables") to a food processing unit through the input/output controllers.

Figure 16:
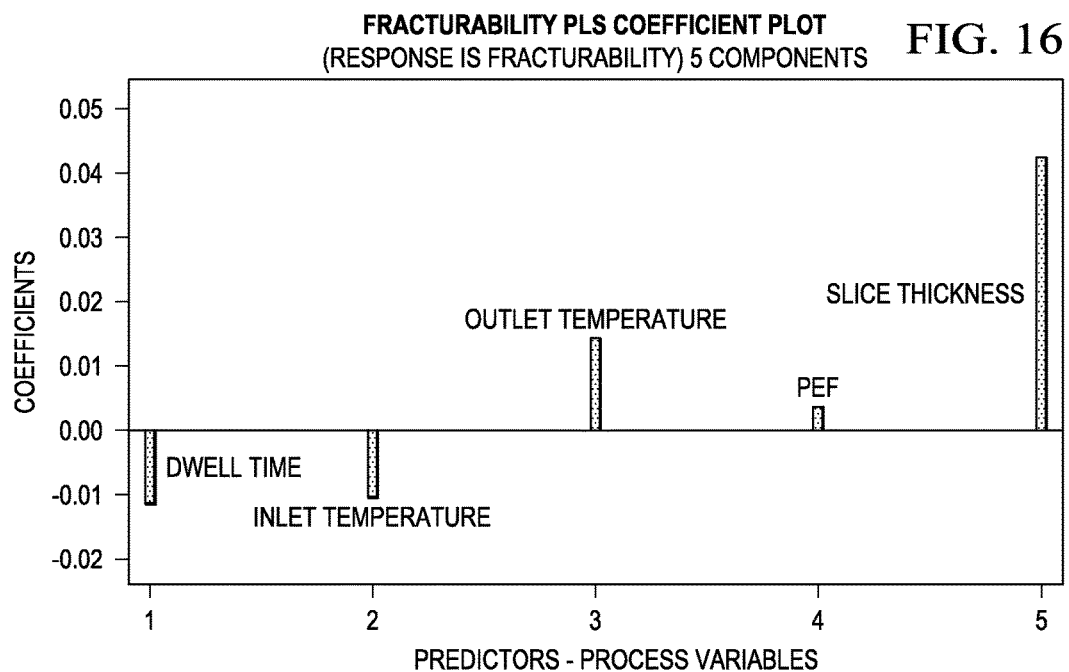
FIG. 16 is an exemplary texture attribute (fracturability) vs. Input parameter correlation chart according to a preferred embodiment of the present invention.

Similarly, in FIG. 16 (1600) a correlation chart of an exemplary texture attribute (fracturability) vs. Input parameter is shown. A model correlating fracturability to input parameters to a food processing unit may be represented by an equation (3) as shown below $$\text{Fracturability} = P_1 B_1 + P_2 B_2 + P_3 B_3 + \ldots P_n B_n \quad (4)$$

Where, $P_n$ is an input parameter $B_n$ is a coefficient associated with the Input parameter $P_n$ (The Coefficients may be positive or negative depending on the direction of correlation).

Depending on a measured fracturability output, the input parameters to a food processing unit may be adjusted to output subsequent food snacks with a fracturability output that is within an acceptable limit. The acceptable limit may be determined based on a correlation of a quantitative acoustic model with a descriptive panel as aforementioned in FIG. 8 (0800).

It should be noted that even though correlation of texture attributes hardness and fracturability have been illustrated in FIG. 15 and FIG. 16, all other texture attributes may be similarly correlated with input parameters.

Exemplary Food Product Manufacturing Feedforward-Feedback System Embodiment (1700)

Figure 17:
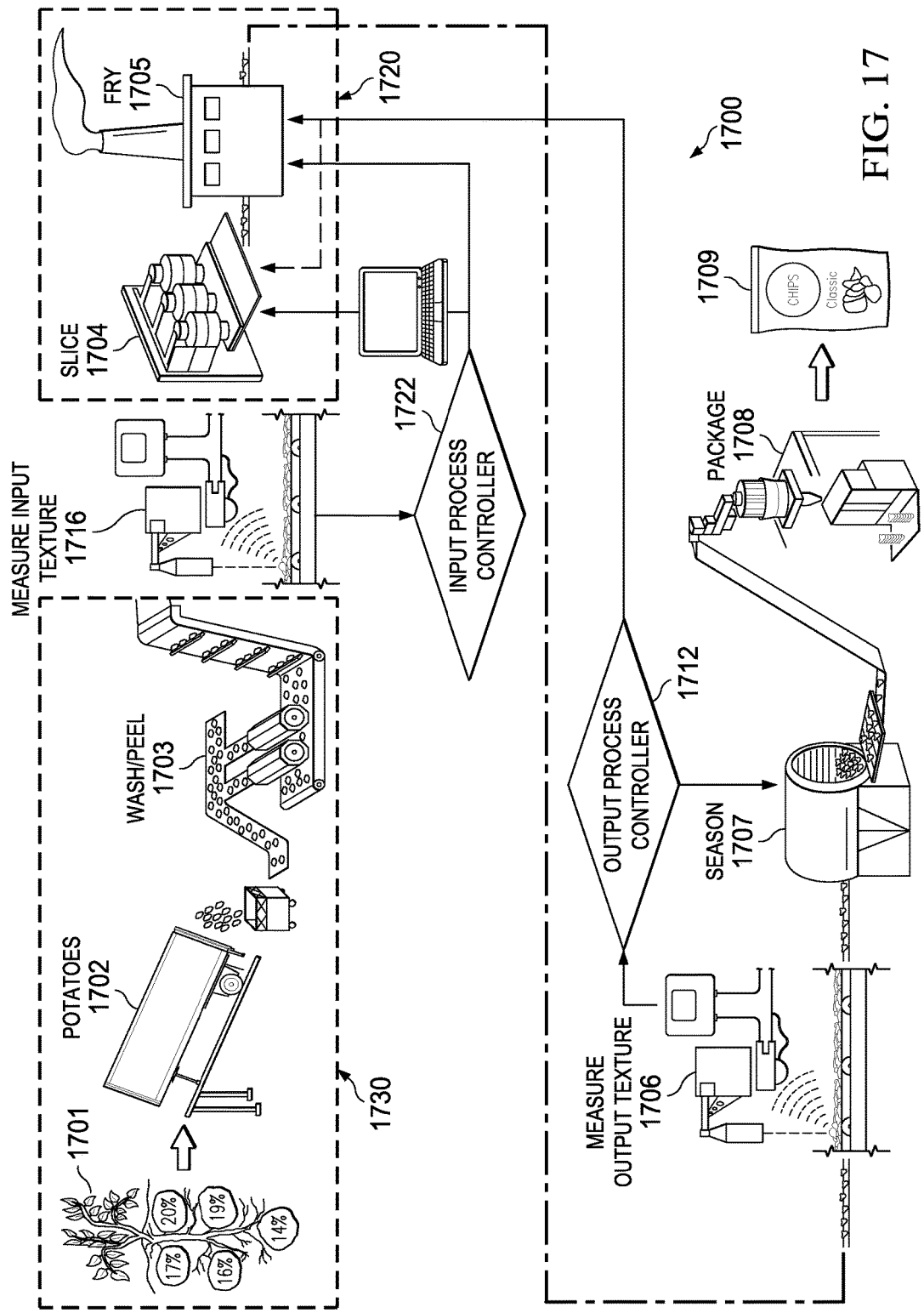
FIG. 17 is an exemplary quantitative texture combined feedback and feedforward manufacturing system according to a preferred embodiment of the present invention.

As generally illustrated in FIG. 17, an exemplary food snack manufacturing feedforward-feedback system comprises an acoustic quantitative texture measurement tool (1706) that is positioned downstream of a food pre-processing unit (FPU) (1730) and upstream of a food processing unit (FPU) (1720). The system (1700) illustrated in FIG. 17 (1700) may be used to manufacture potato chips and other generally manufactured food products such as food snacks. The manufacturing system may comprise a series of inter connected stations that include a sourcing stage (1701), a storage station (1702), wash/peel station (1703), slicing station (1704), frying station (1705), measurement station (1706), a seasoning station (1707), a packaging station (1708) and a labeling station (1709). The food snacks, such as potato chips, may be conveyed from station to station on a conveyor belt in the manufacturing system. The storage station (1702), a food ingredient pre-treatment unit, and the wash/peel station (1703) may be combined as a food pre-processing unit (1730). The food preprocessing unit (1730) may also comprise one or a combination of the storage station (1702), a food ingredient pre-treatment unit, and the wash/peel station (1703). It should be noted that the food preprocessing unit may comprise other processing units ordinarily used in the food snack manufacturing. The FPU (1720) may include one or more of the processing units such as slicing station (1704) and frying station (1705). The texture measurement tool (1706) may be placed between any two stations in the manufacturing process to capture acoustic signals from the passing product after laser excitation. For example the measurement tool (1706) may be placed in between any two stations that may include sourcing stage (1701), storage station (1702), wash/peel station (1703), slicing station (1704), and frying station (1705). The slicing station (1704) may be connected to a slicing process controller (1717) that controls input parameters to the slicing station (1704) such as slicing thickness, moisture control, and slicing ridges. The frying station (1705) may be connected to a fryer process controller (1711) that controls input parameters to the frying station (1705) such as oil input temperature, oil output temperature, oil volume, and frying dwell time. According to a preferred exemplary embodiment, an in-line feed forward control with input acoustic quantitative texture measurement tool enables a consistent manufacturing food texture quality. According to a preferred exemplary embodiment, the acoustic quantitative texture measurement tool (1716) may be positioned immediately downstream of a food preprocessing unit (1730) and upstream of the FPU (1720) and before a seasoning unit (1707) or packaging unit (1708). According to a preferred exemplary embodiment, the input texture measurement tool (1716) records/captures acoustic signal when an energy excitation device such as a laser, strikes the food ingredients from the food preprocessing unit (1730) and processes the acoustic signal to quantitatively measure an input texture attribute with an acoustic model. The energy excitation tool may strike the food product and produce an acoustic signal as aforementioned as exemplary photo acoustic signal method.

The acoustic model may be developed using the method described in FIG. 9 (0900). The model may be programmed into the measuring tool (1716) for measuring one or more input texture attributes of food ingredients such as ingredient solids content, moisture, hardness, density, and slice thickness and model an output texture attribute such as hardness, fracturability and denseness. An model for an expected output texture attribute hardness may be described below:

$$\text{Hardness} = f(Y_{1-n}, Q_{1-n})$$

$$\text{Hardness} = Q_1 D_1 + Q_2 D_2 + Q_3 D_3 + \ldots Q_n D_n \quad (5)$$

Where, $Q_n$ is an intensity associated with a frequency $Y_n$ $D_n$ is a coefficient associated with the frequency $Y_n$ Coefficients ($D_1$-Dn) are determined using the energy excitation method described in FIG. 9 (0900). Coefficients ($D_1$-Dn) may be developed with conventional statistical methods by correlating output texture attributes to input attributes of the food ingredients. For example, in a potato chip manufacturing process, input ingredients such as potatoes may be acoustically modelled for input attributes such as input solids content, moisture, hardness, density, and slice thickness. Potatoes may be procured from various farms and may possess varying attributes. The input measuring tool (1716) measures the attributes of the potatoes and programs an input controller that adjusts process variables to the food processing unit (1720) such that the output texture attribute of the produced potato chips fall within an acceptable limit. The input attributes may be provided to a data processing unit in an input texture measuring tool to determine the coefficients ($D_1$-Dn). A signal processing unit in the texture measurement tool (1716) identifies the relevant frequencies ($Y_n$) and associated intensities ($Q_n$) for the food ingredients. The input measurement tool (1716) may calculate an expected output texture attribute such as hardness from the above model (4) by substituting the coefficients values ($D_1$-Dn) from a stored table (database) for the food product and the intensities ($Q_n$) from the processed acoustic signal. Similarly, other expected output texture attribute such as fracturability and denseness may be calculated from their respective models comprising the respective coefficients. It should be noted that even though the above represented model (4) shows a linear relationship between the texture attribute and intensities, a quadratic or polynomial model may also be represented to calculate the texture attributes.

According to a preferred exemplary embodiment, depending on the measured input attribute, an input controller (1722) may control the output texture attribute of a food product from the FPU (1720). The input controller (1722) may be connected to a slicing input controller and a frying input controller. Typical process control equipment such as PI, PID control devices, may be used to program the input parameters of the slicing station (1704) and frying station (1705). For example, if the expected output texture attribute based on a measured input attribute (hardness), falls outside an acceptable limit, the input controller (1722) may program an input parameter or a combination of input parameters (process variables) to the frying unit such as frying temperature or frying time. The input controller (1722) may program an input parameter to the slicing unit so that the slices are thinner or thicker depending on the correlation of the output texture attribute to the input attributes. According to a preferred exemplary embodiment, the texture measuring tool (1716) continuously feeds input attribute information to an input controller to program input parameters to the food processing unit (1720) such that the expected output texture attribute of the food product falls within an acceptable limit. The acceptable limit may be determined by correlating the acoustic model and a descriptive panel number. A tighter acceptable limit may indicate a more controlled quality process. The acceptable limit may also be further tuned as more data is collected. Each texture attribute may have its own acceptable limits. The measured texture attributes may be monitored continuously and charted for sustaining process quality control. A statistical process control chart may be used to monitor and control a texture attribute with an upper limit and a lower limit. Any trends and outliers from the statistical process control chart may be used to correct, adjust and detect potential issues with the processing units.

Furthermore, an output texture measurement tool (1706) similar to the measurement tool (1306) as aforementioned in FIG. 13 (1300) may be positioned downstream of food processing unit (1720). As the food products such as food snacks travel on a conveyor belt pass from the FPU (1720) to the seasoning station (1707), the excitation tool in the output texture measurement tool (1706) may strike the food snack repeatedly for a set period of time. According to a preferred exemplary embodiment, the excitation tool may continuously strike the food snack for a period of 10 nanoseconds. According to a yet another preferred exemplary embodiment, the excitation tool may continuously strike the food snack for a period of 10 seconds segments. According to a more preferred exemplary embodiment, the excitation tool may continuously strike the food snack for a period of 1 second to 10 seconds. According to a most preferred exemplary embodiment, the excitation tool may continuously strike the food snack for a period of 10 seconds. The excitation tool may strike a particular food snack on the conveyor belt repeatedly so that multiple acoustic signals are generated for the entire surface of the food snack. According to a more preferred exemplary embodiment, the excitation tool may continuously strike the food snack at an average of times per second. It is known that the texture attribute may not be uniform across the entire surface. The excitation energy may strike the food snack across the entire area of the food snack so that any imperfections such as blisters may be detected after the signal has been processed. According to a preferred exemplary embodiment, repeatable measurements for a period of time, enables the measurement tool to identify subtle variations across the entire surface of a food snack. The signal may be captured/recorded by an acoustic capturing device in the output texture measurement tool (1706).

According to a preferred exemplary embodiment, depending on the measured texture attribute, an output controller (1712) may control the output texture attribute of a food product from the FPU (1720). The output controller (1712) may be connected to a slicing input controller and a frying input controller. Typical process control equipment such as PI, PID control devices, may be used to control the input parameters of the slicing station (1704) and frying station (1705). For example, if the texture attribute, hardness, falls outside an acceptable limit, the output controller (1712) may adjust an input parameter to the frying unit such as frying temperature or frying time. The output controller (1712) may adjust an input parameter to the slicing unit so that the slices are thinner or thicker depending on the correlation of the output texture attribute to the input parameters. According to a preferred exemplary embodiment, the texture measuring tool (1706) continuously feeds back information to control input parameters to the food processing unit (1720) such that the texture attribute of the food product falls within an acceptable limit. The acceptable limit may be determined by correlating the acoustic model and a descriptive panel number. A tighter acceptable limit may indicate a more controlled quality process. The acceptable limit may also be further tuned as more data is collected. Each texture attribute may have its own acceptable limits. The measured texture attributes may be monitored continuously and charted for sustaining process quality control.

According to a preferred exemplary embodiment, the output texture measurement tool may heuristically train the input measurement tool such that the output texture attributes of the food product from the food processing unit is tightly controlled. The output texture measurement tool (1706) may feed information to input texture measurement tool (1716) so that the input parameters (process variables) to the food processing unit are continuously adjusted in order to tightly control the output texture attribute. This is especially important as new batches of food ingredients with varying attributes are input to the food preprocessing unit that may impact the output texture of the food product. The continuous feedforward and feedback loop enable a substantially tighter control on the output texture in addition to significant reduction of wastage due to unacceptable texture of the produced food product. According a preferred exemplary embodiment, the tighter control limits may be within +−20% of the output texture attribute limit. According to a more preferred exemplary embodiment, the tighter control limits may be within +−10% of the output texture attribute limit. According to a most preferred exemplary embodiment, the tighter control limits may be within +−5% of the output texture attribute limit.

Exemplary Food Product Manufacturing Method Embodiment (1800)

Figure 18:
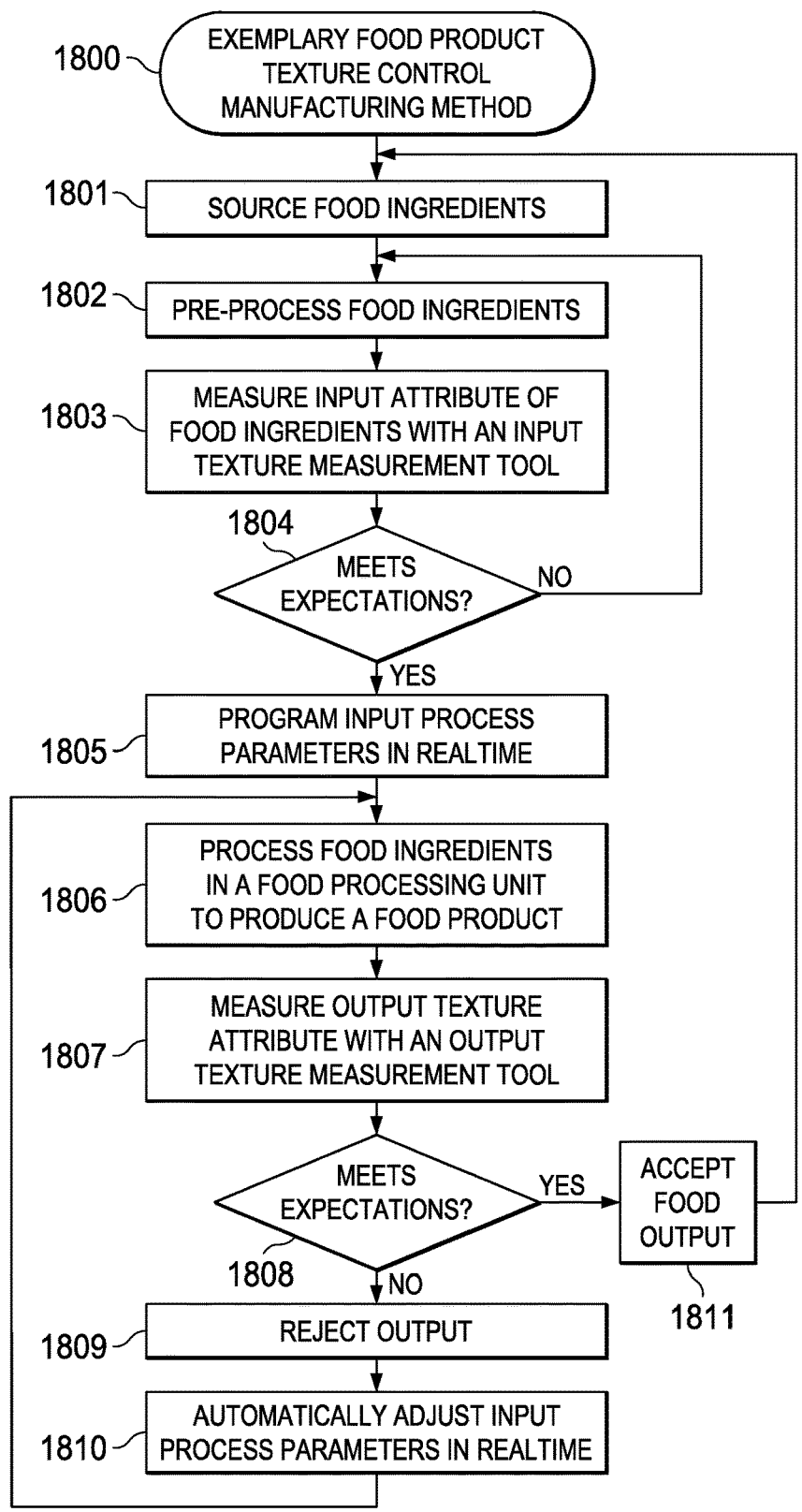
FIG. 18 is an exemplary quantitative texture combined feedback and feedforward manufacturing method according to a preferred embodiment of the present invention.

As generally shown in FIG. 18, a an exemplary feed forward and feedback manufacturing method associated with the feedback manufacturing system in FIG. 17 may include the steps comprising:
(1) Sourcing food ingredients (1801);
  The food ingredients may be potatoes that may be procured from different sources.
(2) pre-processing food ingredients in a food pre-processing unit (1802);
(3) measuring an input attribute of the food ingredients with an input texture measuring tool (1803);
(4) with an input texture measuring tool, determining if an expected output texture attribute based on the measured input attribute is within an acceptable limit, if not, rejecting the input food ingredients and proceeding to step (2) (1804);
  The input attribute may be food properties such as moisture, solids content, oil content, slice thickness, density of solids, topicals, seasonings such as sodium chloride and any flavors/seasonings with particle sizes between 100 microns and 500 microns may be measured in addition to the texture attribute.
(5) program input parameters (process variables) to a food processing unit (1805);
(6) processing food ingredients in a food processing unit to produce a food product (1806);
(7) measuring output texture attribute with an output texture measuring tool (1807);
(8) determining if the output texture attribute is within an acceptable limit, if so, proceeding to step (11) (1808);
(9) if the texture attribute is outside an acceptable limit in step (1808), rejecting the food product (1809);
(10) feeding back output texture attribute information to a controller to adjust input parameters to the food processing unit, proceeding to step (6) (1810); and
(11) accepting the food product and proceeding to step (1) (1811).

This general method summary may be augmented by the various elements described herein to produce a wide variety of invention embodiments consistent with this overall design description.

As generally illustrated in FIG. 19, an exemplary texture attribute Intensity (dB) (1901) vs. relevant frequencies (1902) chart for a food snack treated with various input conditions. Plot (1914), (1915), (1916) are frequency vs Intensity graphs for a potato chip with different solid content, moisture content and hardness of the input ingredients such as potatoes. For example, a plot (1914) may be a frequency vs intensity plot for a food snack that has a different solids content in the input ingredients. Similarly, a plot (1915) may be a frequency vs intensity plot for a food snack that has a different moisture content and different hardness in the input ingredients respectively. A plot (1906) may be plotted for background noise so that the resulting plot may be compensated for the noise. After identifying the relevant frequencies for a food snack such as a potato chip, an acoustic signal may be captured for each of the input conditions and the acoustic signal may be further processed to determine the intensities associated with the identified frequencies for the food property of the food snack. For example in FIG. 21, an identified frequency 40000 Hz may have an intensity of 75 dB (1903) for plot (1913), an intensity of 74 dB (1904) for plot (1914) and an intensity of 76 dB (1905) for plot (1915). The intensities may be substituted into a food property model generated by aforementioned equation (2) and a food property such as a texture attribute may be calculated. As illustrated in FIG. 21, the 3 different input conditions of the food ingredients (solids content, moisture content and hardness) resulted in 3 different associated intensities which further result in 3 different texture attributes. Therefore, an acoustic signal may be captured and processed for a food product and a texture attribute may be calculated based on the relevant frequencies. The input conditions may be tailored to achieve a desirable texture attribute value that is within a predefined limit. The predefined limit may be correlated to a qualitative descriptive panel number. Similarly, plots may be generated for various food properties by capturing an acoustic signal and processing it. The intensities associated with the various food properties at their respective frequencies may be determined and the food property may be calculated. A model may be generated for each of the food properties through signal processing and statistical regression as aforementioned. Therefore, a photo acoustic method may be used to identify differences in a food product based on any food property such as a texture attribute, solids content, moisture, oil content, density, blister density and elements such as Sodium, Potassium, Calcium, and Magnesium. The differences in the food product may be as minor as +−5% of the desirable value. For example, a desirable hardness value of 75 may be differentiated from a hardness value of 70 that may be undesirable for the food product. The food product with the undesirable value (70) may be rejected and not further processed or packaged.

Texture Feedback Control System Summary

The present invention system anticipates a wide variety of variations in the basic theme of a feedback system for controlling texture of a food product in a continuous manufacturing process, wherein the system comprises:
- a food pre-processing unit;
- a food processing unit;
- a texture measuring tool positioned downstream from the food processing unit, wherein the texture measuring tool is configured to quantitatively measure a texture attribute of the food product that is output from the food processing unit by use of a laser to excite a portion of a food product and an acoustic capturing device to capture an acoustic signal generated by the laser excitation; and
- a controller, the controller controlling a plurality of input parameters to the food processing unit and the food pre-processing unit based on input from the texture measuring tool.

This general system summary may be augmented by the various elements described herein to produce a wide variety of invention embodiments consistent with this overall design description.

Texture Feedback Method Summary

The present invention method anticipates a wide variety of variations in the basic theme of implementation, but can be generalized as a feedback control method of texture in the manufacturing of food products, the method comprises the steps of:
(1) processing food ingredients in a food processing unit to produce the food product;
(2) measuring a texture attribute of the food product with a texture measuring tool;
(3) determining if the texture attribute is within an acceptable limit, if so, proceeding to step (6);
(4) if the texture attribute is outside an acceptable limit in step (3), rejecting the food product;
(5) feeding back information to the food processing unit to adjust input parameters to the food processing unit, proceeding to step (1); and
(6) accepting the food product and proceeding to step (1).

System/Method Variations

The present invention anticipates a wide variety of variations in the basic theme of texture measurement. The examples presented previously do not represent the entire scope of possible usages. They are meant to cite a few of the almost limitless possibilities.

This basic system and method may be augmented with a variety of ancillary embodiments, including but not limited to:
- An embodiment wherein the controller utilizes the texture attribute information to control the plurality of input parameters to the food processing unit the food pre-processing unit such that a texture attribute of a resultant food product output from the food processing unit falls within an acceptable limit.
- An embodiment wherein the texture attribute is selected from a group comprising: hardness, fracturablity, denseness, crispiness, tooth-pack, surface roughness, oily mouthfeel, surface oiliness, moistness of mass, roughness of mass, and residual greasiness.
- An embodiment wherein the food product is a starch based food snack.
- An embodiment wherein the food product is a potato chip.
- An embodiment 1 wherein the acoustic capturing device is a microphone; the microphone is configured to be wired to a data processing unit in the texture measuring tool.
- An embodiment wherein the acoustic capturing device is a microphone; the microphone is configured to wirelessly connect with a data processing unit in the texture measuring tool.
- An embodiment wherein the acoustic capturing device is configured to capture the acoustic signal within the frequency range of 0 to 200 kHz.
- An embodiment wherein the acoustic capturing device is configured to capture the acoustic signal in a single direction.
- An embodiment wherein the acoustic capturing device is configured to capture sound waves in all directions.

One skilled in the art will recognize that other embodiments are possible based on combinations of elements taught within the above invention description.

Texture Feedforward Control System Summary

The present invention system anticipates a wide variety of variations in the basic theme of a feedforward system for controlling texture of a food product in a continuous manufacturing process, wherein the system comprises:
- a food pre-processing unit;
- a food processing unit;
- a texture measuring tool positioned downstream from the food pre-processing unit, wherein the texture measuring tool is configured to quantitatively measure an input attribute of food ingredients that are input to the food pre-processing unit by use of a laser to excite a portion of the food ingredients and an acoustic capturing device to capture the acoustic signal generated by the laser excitation; and
- a controller, the controller controlling a plurality of input parameters to the food processing unit and the food pre-processing unit based on input from the texture measuring tool.

This general system summary may be augmented by the various elements described herein to produce a wide variety of invention embodiments consistent with this overall design description.

Texture Feedforward Method Summary

The present invention method anticipates a wide variety of variations in the basic theme of implementation, but can be generalized as a feedforward control method of texture in the manufacturing of food products, the method comprises the steps of:

(1) measuring an input texture attribute of food ingredients with an input texture measuring tool;
(2) determining if the input texture attribute value is within an acceptable input limit, if so, proceeding to step (4);
(3) rejecting the food ingredients and proceeding to step (1);
(4) programming plural input parameters to a food processing unit based on the input texture attribute value;
(5) producing food product from the food processing unit; and
(6) measuring an output texture attribute and proceeding to step (1).

What is claimed is:

1. A feedback system for controlling texture attribute of a food product in a continuous manufacturing process, wherein said system comprises:
    a food pre-processing unit;
    a food processing unit downstream from said food pre-processing unit;
    a texture measuring tool positioned downstream from said food processing unit, said texture measuring tool further comprising:
        a housing;
        a laser generator attached to said housing;
        an acoustic capturing device proximally located to said housing;
        a data processing unit in communication with at least said acoustic capturing device;
        wherein a laser from said laser generator is directed to non-invasively strike an exterior surface of said food product after its output from said food processing unit, the striking heating the struck surface sufficient to cause rapid thermal expansion of the struck exterior surface thereby producing an acoustic signal to be detected by said acoustic capturing device;
        wherein said data processing unit is configured to non-invasively and quantitatively measure said texture attribute of said output food product based on input from said acoustic capturing device generated based on said detected acoustic signal; and
        a controller, said controller controlling a plurality of input parameters to said food processing unit and said food pre-processing unit based on input from said texture measuring tool.

2. The feedback system of claim 1 wherein said controller utilizes said texture attribute information to control said plurality of input parameters to said food processing unit and said food pre-processing unit such that a texture attribute of a resultant food product output from said food processing unit falls within an acceptable limit.

3. The feedback system of claim 1 wherein said food product is moving on a production line when said laser strikes said food product.

4. The feedback system of claim 1 wherein said food product is stationary on a production line when said laser strikes said food product.

5. The feedback system of claim 1 wherein said texture attribute is selected from a group comprising: hardness, fracturability, denseness, crispiness, tooth-pack, surface roughness, oily mouthfeel, surface oiliness, moistness of mass, roughness of mass, and residual greasiness.

6. The feedback system of claim 1 wherein said food product is a starch based food snack.

7. The feedback system of claim 1 wherein said food product is a potato chip.

8. The feedback system of claim 1 wherein said acoustic capturing device is a microphone; said microphone is configured to be wired to said data processing unit in said texture measuring tool.

9. The feedback system of claim 1 wherein said acoustic capturing device is a microphone; said microphone is configured to wirelessly connect with said data processing unit in said texture measuring tool.

10. The feedback system of claim 1 wherein said acoustic capturing device is configured to capture said acoustic signal within the frequency range of 0 to 200 kHz.

11. The feedback system of claim 1 wherein said acoustic capturing device is configured to capture said acoustic signal in a single direction.

12. The feedback system of claim 1 wherein said acoustic capturing device is configured to capture sound waves in all directions.

13. The feedback system of claim 1 wherein said food pre-processing unit is selected from a group comprising: storage station, a food ingredient pre-treatment unit, a peel station or a wash station.

14. The feedback system of claim 1 wherein said food processing unit is selected from a group comprising: a frying station, a seasoning station or a slicing station.

15. The feedback system of claim 1 wherein said input parameters are selected from a group comprising: oil input temperature, oil output temperature, oil volume, frying dwell time, slicing thickness, moisture control, or slicing ridges.

16. A feedforward system for controlling texture of a food product in a continuous manufacturing process, wherein said system comprises:
    a food pre-processing unit;
    a food processing unit;
    a texture measuring tool positioned downstream from said food pre-processing unit, said texture measuring tool further comprising:
        a housing;
        a laser generator attached to said housing;
        an acoustic capturing device proximally located to said housing;
        a data processing unit in communication with at least said acoustic capturing device;
        wherein a laser from said laser generator is directed to non-invasively strike an exterior surface of a food ingredient to be input to said food pre-processing unit, the striking heating the struck surface sufficient to cause rapid thermal expansion of the struck exterior surface thereby producing an acoustic signal to be detected by said acoustic capturing device;
        wherein said data processing unit is configured to quantitatively and non-invasively measure an input attribute of said food ingredient to be input based on input from said acoustic capturing device generated based on said detected acoustic signal; and
    a controller, said controller controlling a plurality of input parameters to said food processing unit and said food pre-processing unit based on input from the texture measuring tool.

17. The feedforward system of claim 16 wherein said controller utilizes said input attribute information to control said plurality of input parameters to said food processing unit and said food pre-processing unit such that a texture attribute of a resultant food product output from said food processing unit falls within an acceptable limit.

18. The feedforward system of claim 17 wherein said texture attribute is selected from a group comprising: hardness, fracturability, denseness, crispiness, tooth-pack, surface roughness, oily mouthfeel, surface oiliness, moistness of mass, roughness of mass, and residual greasiness.

19. The feedforward system of claim 16 wherein said input attribute is selected from a group comprising: moisture, solids content, density, and hardness.

20. The feedforward system of claim 16 wherein said food pre-processing unit is selected from a group comprising: storage station, a food ingredient pre-treatment unit, a peel station or a wash station.

21. The feedforward system of claim 16 wherein said food processing unit is selected from a group comprising: a frying station, a seasoning station or a slicing station.

22. The feedforward system of claim 16 wherein said input parameters are selected from a group comprising: oil input temperature, oil output temperature, oil volume, frying dwell time, slicing thickness, moisture control, or slicing ridges.

* * * * *